(12) United States Patent
Madadi et al.

(10) Patent No.: US 9,938,246 B2
(45) Date of Patent: Apr. 10, 2018

(54) DISUBSTITUTED TRIAZOLE ANALOGS

(71) Applicants: Nikhil Reddy Madadi, Little Rock, AR (US); Narsimha Reddy Penthala, Little Rock, AR (US); Peter Crooks, Little Rock, AR (US); Leena Maddukuri, Little Rock, AR (US); Robert Eoff, Little Rock, AR (US)

(72) Inventors: Nikhil Reddy Madadi, Little Rock, AR (US); Narsimha Reddy Penthala, Little Rock, AR (US); Peter Crooks, Little Rock, AR (US); Leena Maddukuri, Little Rock, AR (US); Robert Eoff, Little Rock, AR (US)

(73) Assignee: BIOVENTURES, LLC, Little Rock, AR (US)

( * ) Notice: Subject to any disclaimer, the term of this patent is extended or adjusted under 35 U.S.C. 154(b) by 0 days.

(21) Appl. No.: 15/282,312

(22) Filed: Sep. 30, 2016

(65) Prior Publication Data

US 2017/0015635 A1 Jan. 19, 2017

Related U.S. Application Data

(63) Continuation-in-part of application No. PCT/US2015/023628, filed on Mar. 31, 2015.

(60) Provisional application No. 61/972,938, filed on Mar. 31, 2014.

(51) Int. Cl.
*C07D 249/06* (2006.01)
*C07D 401/04* (2006.01)
*C07D 405/04* (2006.01)
*C07D 409/04* (2006.01)

(52) U.S. Cl.
CPC ......... *C07D 249/06* (2013.01); *C07D 401/04* (2013.01); *C07D 405/04* (2013.01); *C07D 409/04* (2013.01)

(58) Field of Classification Search
None
See application file for complete search history.

(56) References Cited

U.S. PATENT DOCUMENTS

| | | |
|---|---|---|
| 3,642,813 A | 2/1972 | Rudolf et al. |
| 5,484,940 A | 1/1996 | Grant et al. |
| 9,597,316 B2 | 3/2017 | Penthala et al. |
| 2004/0248950 A1 | 12/2004 | Shizuka et al. |
| 2007/0238699 A1 | 10/2007 | Demko et al. |
| 2008/0113993 A1 | 5/2008 | De Belin et al. |
| 2009/0253656 A1 | 10/2009 | Yamazaki et al. |
| 2010/0081678 A1 | 4/2010 | Crooks et al. |
| 2010/0144734 A1 | 6/2010 | Hou et al. |
| 2011/0053941 A1 | 3/2011 | Mautino et al. |
| 2011/0077250 A1 | 3/2011 | Ryder |
| 2011/0144139 A1 | 6/2011 | Vasioukhin et al. |
| 2011/0251236 A1 | 10/2011 | Lai et al. |
| 2015/0328216 A1 | 11/2015 | Penthala et al. |
| 2016/0068506 A1 | 3/2016 | Penthala et al. |
| 2016/0075689 A1 | 3/2016 | Penthala et al. |

FOREIGN PATENT DOCUMENTS

| | | |
|---|---|---|
| DE | 1944419 A1 | 3/1971 |
| DE | 3410700 A1 | 9/1985 |
| EP | 0754682 A1 | 1/1997 |
| EP | 1921072 A1 | 5/2008 |
| JP | 2012208173 A | 10/2012 |
| WO | 1992004334 A1 | 3/1992 |
| WO | 2000035865 A2 | 6/2000 |
| WO | 2001093841 A2 | 12/2001 |
| WO | 2003042207 A1 | 5/2003 |
| WO | 2008131320 A1 | 10/2008 |
| WO | 2010150211 A2 | 12/2010 |
| WO | 2011127192 A2 | 10/2011 |
| WO | 2014105957 A1 | 7/2014 |
| WO | 2014172363 A2 | 10/2014 |
| WO | 2014176351 A1 | 10/2014 |
| WO | 2015153635 A1 | 10/2015 |

OTHER PUBLICATIONS

George, MV. et al. Oxidation of Phenylhydrazones with Manganese Dioxide. Journal of Organic Chemistry. 1967, vol. 32, p. 2255.*
Khadem, HE. et al. Reactions of Benzil Mono- and Bis-arylhydrazones. Journal of the Chemical Society. 1968, vol. 8, p. 950.*
Grundon, MF. et al. The Reactions of Hydrazones and Related Compounds with Strong Bases. Part 4. 4,5-Diaryl-1,2,3-triazoles from Aromatic Aldehyde Azines and from the Reaction of Arenecarbonitriles with Aryldiazomethanes. Journal of the Chemical Society Perkin Trans. 1988, vol. 1, p. 2917.*
Carta, A. et al., "3-Aryl-2-[1H-benzotriazol-1-yl]acrylonitriles: A novel class of potent tubulin inhibitors," Eur. J. Med. Chem., Jun. 11, 2011, pp. 4151-4167, vol. 46, No. 9, Elsevier Masson SAS, Paris, France.
Coggins, G. et al., "N-Aroyl Indole Thiobarbituric Acids as Inhibitors of DNA Repair and Replication Stress Response Polymerases," NIH Public Access, Author Manuscript, available in PMC Aug. 16, 2014, pp. 1-19, published in final edited form as: ACS Chem Biol., Aug. 16, 2013, pp. 1722-1729, vol. 8, No. 8.
Corrected Search Report and Written Opinion dated Oct. 12, 2016 from related Singaporean Patent Application No. 11201508054U; 11 pgs.
Dhayalan, V. et al., "Studies on Lewis-acid mediated domino reaction of N-protected bromomethylindoles with arenes/heteroarenes," Indian Journal of Chemistry, Jun. 2011, pp. 843-857, vol. 50B.
Extended European Search Report dated May 12, 2016 from related European Patent Application No. 13868363.6; 6 pgs.

(Continued)

*Primary Examiner* — Niloofar Rahmani
(74) *Attorney, Agent, or Firm* — Polsinelli PC

(57) ABSTRACT

The present invention relates to disubstituted triazoles, their synthesis, and their use as anti-cancer compounds. In particular, compounds of Formula (I) are provided.

11 Claims, 14 Drawing Sheets
(6 of 14 Drawing Sheet(s) Filed in Color)

(56) References Cited

OTHER PUBLICATIONS

Extended European Search Report dated Jan. 12, 2017 from related European Patent Application No. 14785256.0; 14 pgs.
Extended European Search Report dated Oct. 18, 2016 from related European Patent Application No. 14788020.7; 12 pgs.
Haldar, M. et al., "Synthesis of barbiturate-based methionine aminopeptidase-1 inhibitors," Bioorg. Med. Chem. Lett., Feb. 27, 2008, pp. 2373-2376, 2008, vol. 18, Elsevier Ltd.
International Search Report and Written Opinion dated Apr. 22, 2014 from related International Patent Application No. PCT/US2013/077812; 10 pgs.
International Search Report and Written Opinion dated Sep. 11, 2014 from related International Patent Application No. PCT/US2014/035169; 7 pgs.
International Search Report and Written Opinion dated Nov. 7, 2014 from related International Patent Application No. PCT/US2014/034185; 13 pgs.
International Search Report and Written Opinion dated Aug. 25, 2015 from related International Patent Application No. PCT/US2015/023628; 11 pgs.
Jalily, P. et al., "Novel cyanocombretastatins as potent tubulin polymerization inhibitors," Bioorg. Med. Chem. Lett., Sep. 7, 2012, pp. 6731-6734, vol. 22, No. 21, Elsevier Ltd.
Kaur, J. et al., "N-1 and C-3 substituted indole Schiff bases as selective COX-2 inhibitors: Synthesis and biological evaluation," Bioorg. Med. Chem. Lett., Feb. 6, 2012, pp. 2154-2159, vol. 22, Elsevier Ltd.
Kubinyi, E. "3D QSAR in Drug Design Theory Methods and Applications: Ligand-Protein Interactions and Molecular Similarity," Springer, 1998, pp. 243-244, vol. 2-3.
Madadi, N. et al., "Synthesis and anti-proliferative activity of aromatic substituted 5-((1-benzyl-1H-indol-3-yl)methylene)-1,3-dimethylpyrimidine-2,4,6(1H,3H,5H)-trione analogs against human tumor cell lines," NIH Public Access, Author Manuscript, available in PMC Jan. 15, 2015, pp. 1-10, Published in final edited form as: Bioorg. Med. Chem. Lett., Jan. 15, 2014, pp. 601-603, vol. 24, No. 2, Elsevier Ltd.
Magarian, E. et al., "New Compounds: Acrylonitrile Derivatives as Potential Antineoplastic Agents," Journal of Pharmaceutical Sciences, Sep. 30, 1969, pp. 1166-1167, vol. 58, No. 9.
Mali, J. et al., "An efficient green protocol for the synthesis of 2-aryl substituted benzothiazoles," Green Chemistry Letters and Reviews, Sep. 2010, pp. 209-212, vol. 3, No. 3, Taylor & Francis.
Maya, A. et al., "Further Naphthylcombretastatins. An Investigation on the Role of the Naphthalene Moiety," J. Med. Chem., 2005, pp. 556-568, vol. 48, No. 2, American Chemical Society, United States.
Mekouar, K. et al., "Styrylquinoline Derivatives: A New Class of Potent HIV-1 Integrase Inhibitors That Block HIV-1 Replication in CEM Cells," J. Med. Chem., Jan. 21, 1998, pp. 2846-2857, vol. 41, No. 15, American Chemical Society.
Nguyen, T. et al., "Synthesis and biological evaluation of novel heterocyclic derivatives of combretaatatin A-4," Bioorg. Med. Chem. Lett., Sep. 24, 2012, pp. 7227-7231, vol. 22, No. 23.
Nguyen, T. et al., "Synthesis of (Z) isomers of benzoheterocyclic derivatives of combretastatin A-4: a comparative study of several methods," Tetrahedron, Jan. 9, 2013, pp. 2336-2347, vol. 69, No. 10, Elsevier Science Publishers, Amsterdam, Netherlands.
Notice of Allowance dated Dec. 1, 2016 from related U.S. Appl. No. 14/651,113; 5 pgs.
Office Action dated Jun. 3, 2016 from related U.S. Appl. No. 14/651,113; 9 pgs.
Office Action dated Feb. 14, 2017 from related U.S. Appl. No. 14/785,381; 7 pgs.
Office Action dated Feb. 8, 2016 from related U.S. Appl. No. 14/785,381; 12 pgs.
Office Action dated May 20, 2016 from related U.S. Appl. No. 14/785,381; 11 pgs.
Office Action dated Oct. 31, 2016 from related U.S. Appl. No. 14/785,381; 9 pgs.
Office Action dated Jul. 6, 2016 from related Canadian Patent Application No. 2,910,063; 4 pgs.
Office Action dated Nov. 17, 2016 from related U.S. Appl. No. 14/786,331; 15 pgs.
Ohsumi, K. et al., "Novel Combretastatin Analogues Effective against Murine Solid Tumors: Design and Structure-Activity Relationships," J. Med. Chem., Sep. 7, 1998, pp. 3022-3032, vol. 41, No. 16, American Chemical Society, United States.
Penthala, N. et al., "5-((1-Aroyl-1H-indol-3-yl)methylene)-2-thioxodihydropyrimidine-4,6(1H,5H)-diones as potential anticancer agents with anti-inflammatory properties," Bioorg. Med. Chem. Lett., Mar. 1, 2013, pp. 1442-1446, vol. 23, No. 5, Elsevier Ltd.
Penthala, N. et al., "5-((1-Aroyl-1H-indol-3-yl)methylene)-2-thioxodihydropyrimidine-4,6(1H,5H)-diones as potential anticancer agents with anti-inflammatory properties," NIH Public Access, Author Manuscript, available in PMC Sep. 18, 2014, pp. 1-14, Elsevier Ltd.; Published in final edited form as: Bioorg. Med. Chem. Lett., Mar. 1, 2013, pp. 1442-1446, vol. 23, No. 5.
Penthala, N. et al., "Synthesis and evaluation of a series of benzothiopene acrylonitrile analogs as anticancer agents," NIH Public Access, Author Manuscript, available in PMC Jul. 1, 2014, pp. 1-18; Published in final edited form as: Medchemcomm., Jul. 1, 2013, pp. 1073-1078, vol. 4, No. 7, The Royal Society of Chemistry.
Penthala, N. et al., "Synthesis and In Vitro Screening of Novel Heterocyclic Compounds as Potential Breast Cancer Agents," Breast Cancer—Current and Alternative Therapeutic Modalities, Prof. Esra Gunduz (Ed.), Nov. 2011, Chapter 14, pp. 283-294, ISBN: 978-953-307-776-5, InTech.
Pubchem, Compound Summary for CID 631500, "4,5-diphenyltriazole," Mar. 28, 2005, 4 pgs.
Reddy, Y. et al., "Novel substituted (Z)-5-((N-benzyl-1H-indol-3-yl)methylene)imidazolidine-2,4-diones and 5-((N-benzyl-1H-indol-3-yl)methylene)pyrimdine-2,4,6(1H,3H,5H)-triones as potent radio-sensitizing agents," Bioorg. Med. Chem. Lett., Jan. 15, 2010, pp. 600-602, vol. 20, No. 2, Elsevier Ltd.
Sekhar, K. et al., "The novel chemical entity YTR107 inhibits recruitment of nucleophosmin to sites of DNA damage, suppressing repair of DNA double strand breaks, and enhancing radiosensitization," NIH Public Access, Author Manuscript, available in PMC Oct. 15, 2012, pp. 1-18, published in final edited form as: Clin. Cancer Res., Oct. 15, 2011, pp. 6490-6499, vol. 17, No. 20.
Shaveta, P. et al., "Structural optimization of indole based compounds for highly promising anti-cancer activities: Structure activity relationship studies and identification of lead molecules," European Journal of Medicinal Chemistry, Jan. 8, 2014, pp. 440-450, vol. 74.
Singh, P. et al., "Design, synthesis and anticancer activities of hybrids of indole and barbituric acids—Identification of highly promising leads," Bioorg. Med. Chem. Lett., Apr. 9, 2009, pp. 3054-3058, vol. 19, No. 11, Elsevier, Ltd.
Supplementary Partial Search Report dated Oct. 6, 2016 from related European Patent Application No. 14785256.0; 8 pgs.
Wermuth, "The Practice of Medicinal Chemistry," 2d. Ed., 2003, Chapters 9-10, pp. 131-157, Elsevier.
Penthala, N. et al., "(Z)-3-(1H-indol-3-yl)-2-(3,4,5-trimethoxyphenyl)acrylonitrile," Acta Crystallographica Section E, Feb. 17, 2012, p. o729, vol. E68, with Supporting Information, pp. sup1-sup7.
Perez-Melero, C. et al., "A new family of quinolone and quinoxaline analogues of combretastatins," Bioorg. Med. Chem. Lett., May 25, 2004, pp. 3771-3774, vol. 14, Elsevier Ltd.
Saczewski, F. et al., "Synthesis, X-ray Crystal Structures, Stabilities, and in Vitro Cytotoxic Activities of New Heteroarylacrylonitriles," J. Med. Chem., 2004, pp. 3438-3449, vol. 47, No. 13, American Chemical Society.
Sonar, V. et al., "(E)-3-(Benzo[b]thiophen-2-yl)-2-(3,4,5-trimethoxyphenyl)acrylonitrile and (Z)-3-(benzo[b]thiophen-2-yl)-2-(3,4-dimethoxyphenyl)acrylonitrile," Acta Crystallographica Section C, Nov. 24, 2007, pp. o743-o745, vol. C63, International Union of Crystallography.
Butler, R. et al., "A Ceric Ammonium Nitrate N-Dearylation of N-p-Anisylazoles Applied to Pyrazole, Triazole, Tetrazole, and Pentazole Rings: Release of Parent Azoles. Generation of Unstable

(56) References Cited

OTHER PUBLICATIONS

Pentazole, HN5/N5-, in Solution,"J. Org. Chem., Feb. 2008, pp. 1354-1364, vol. 73, No. 4, American Chemical Society, USA.

Extended European Search Report dated Aug. 3, 2017 from related European Patent Application No. 15773146.4; 12 pgs.

Hou, D-R. et al., "1,2,3-Triazole derivatives as new cannabinoid CB1 receptor antagonists," Bioorg. Med. Chem. Lett., 2009, pp. 1022-1025, vol. 19, No. 3, Elsevier Ltd.

Hu, J-R. et al., "A one-pot synthesis of bisarylhydrazones by Cu(I)-catalyzed aerobic oxidation," Tetrahedron, 2013, pp. 9865-9869, vol. 69, No. 46, Elsevier Ltd.

Kim, D-K. et al., "Synthesis and biological evaluation of novel 2-pyridinyl-[1,2,3]triazoles as inhibitors of transforming growth factor beta1 type 1 receptor," Bioorg. Med. Chem. Lett., May 17, 2004, pp. 2401-2405, vol. 14, No. 10, Elsevier Ltd.

Odlo, K. et al., "1,5-Disubstituted 1,2,3-triazoles as cis-restricted analogues of combretastatin A-4: Synthesis, molecular modeling and evaluation as cytotoxic agents and inhibitors of tubulin," Bioorg. Med. Chem., May 1, 2008, pp. 4829-4838, vol. 16, No. 9, Pergamon, Great Britain.

Ohsumi, K. et al., "Sytheses and Antitumor Activity of Cis-Restricted Combretastatins: 5-Membered Heterocyclic Analogues," Bioorg. Med. Chem. Lett., Nov. 17, 1998, pp. 3153-3158, vol. 8, No. 22, Pergamon, Netherlands.

Oliva, C. et al., "N-Substituted-1,2,3-triazoles: synthesis, characterization and evaluation as cannabinoid ligands," ARKIVOC, 2010, pp. 127-147, vol. (ii), ARKAT USA, Inc.

Papudippu, M. et al., "Regioselective sythesis and cannabinoid receptor binding affinity of N-alkylated 4,5-diaryl-1,2,3-triazoles," Med. Chem. Res., Feb. 22, 2012, pp. 4473-4484, vol. 21, No. 12, Springer Science+Business Media, LLC.

Romagnoli, R. et al., "Synthesis and Antitumor Activity of 1,5-Disubstituted 1,2,4-Triazoles as Cis-Restricted Combretastatin Analogues,"NIH Public Access Author Manuscript, available in PMC May 27, 2011, pp. 1-27, published in final edited form as: J. Med. Chem., May 27, 2010, pp. 4248-4258, vol. 53, No. 10, American Chemical Society.

Tome, A. (Ed.), "Product class 13: 1,2,3-triazoles," Science of Sythesis: Hetarenes and Related Ring Systems Five-Membered Hatarenes with Three or More Heteroat; Methods of Molecular Transformations, Jan. 1, 2004, pp. 415-601, vol. 13, Category 2, Stuttgart, Georg Theime Verlag, Germany.

Wang, X-j. et al., "General Solution to the Synthesis of N-2-Substituted 1,2,3-Triazoles," Org. Lett., Oct. 15, 2010, pp. 4632-4635, vol. 12, No. 20, American Chemical Society.

* cited by examiner

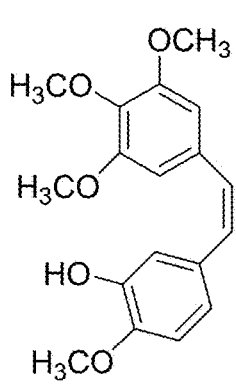
1
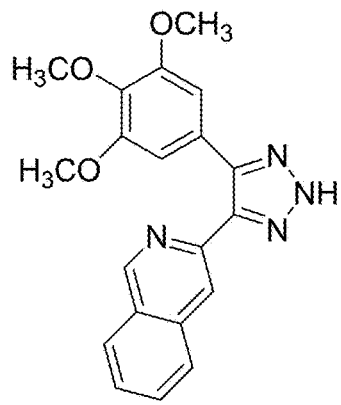
Example 3
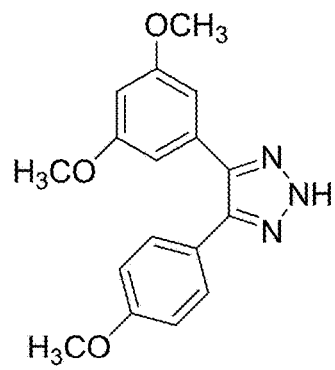
Example 4
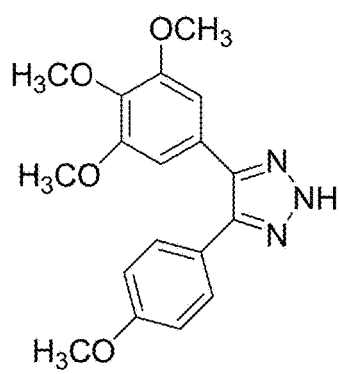
Example 5
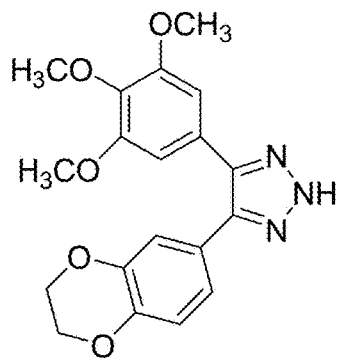
Example 6
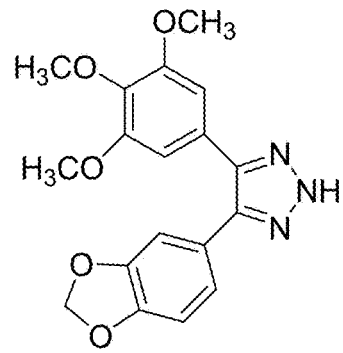
Example 7
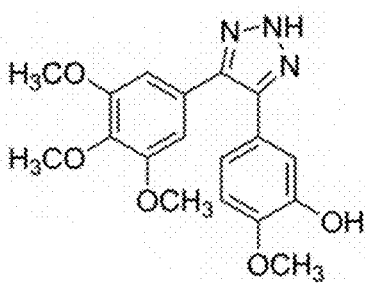
Example 8
FIG. 1

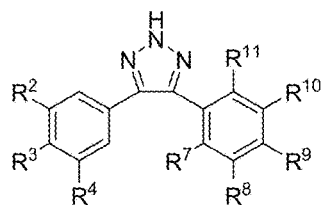

$R^2 = R^3 = R^4 = R^8 = R^9 = R^{10} = OCH_3, R^7 = R^{11} = H$
$R^2 = R^3 = R^4 = R^9 = OCH_3, R^8 = OH, R^7 = R^{11} = R^{10} = H$
$R^2 = R^4 = R^9 = OCH_3, R^7 = R^{11} = R^{10} = R^3 = R^8 = H$
$R^2 = R^3 = R^4 = R^9 = OCH_3, R^7 = R^5 = R^{10} = R^8 = H$
$R^2 = R^3 = R^4 = OCH_3, R^9 = NO_2, R^7 = R^{11} = R^{10} = R^8 = H$
$R^2 = R^4 = OCH_3, R^5 = NO_2, R^7 = R^{11} = R^{10} = R^3 = R^8 = H$
$R^3 = R^4 = R^8 = R^9 = OCH_3, R^7 = R^{11} = R^{10} = R^3 = R^2 = H$
$R^3 = R^4 = OCH_3, R^8 = R^9 = Cl, R^7 = R^{11} = R^{10} = R^2 = H$
$R^2 = R^4 = Br, R^7 = OCH_3, R^8 = R^{11} = R^{10} = R^3 = R^9 = H$

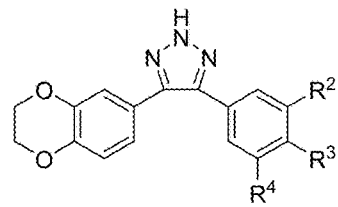

$R^2 = R^3 = R^4 = OCH_3$
$R^2 = R^3 = OCH_3, R^4 = H$
$R^3 = NO_2, R^2 = R^4 = H$

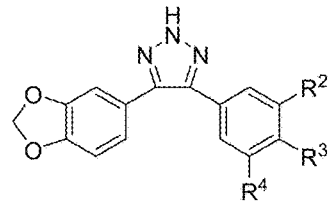

$R^2 = R^3 = R^4 = OCH_3$
$R^2 = R^3 = OCH_3, R^4 = H$
$R^3 = NO_2, R^2 = R^4 = H$
$R^2 = R^3 = R^4 = H$

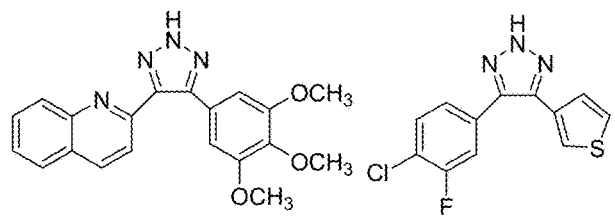

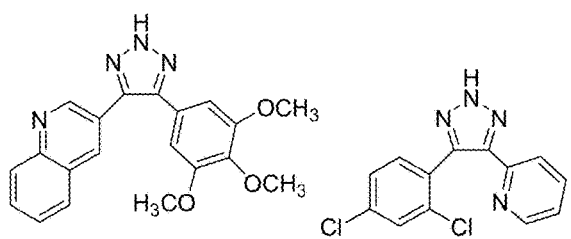

FIG. 2

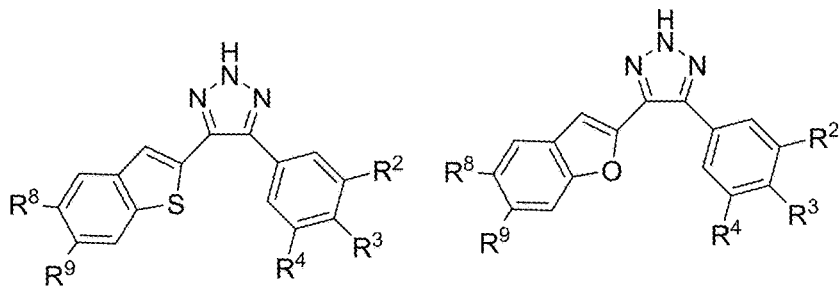

R²=R³=OCH₃, R⁴=H
R²=R⁴=OCH₃, R³=H
R²=R³=R⁴=OCH₃
R²=R⁴=H, R³=OCH₃
R²=R⁴=OCH₃, R³=OH
R²=R⁴=H, R³=OH
R⁸=F, Cl, Br, CN, OH, OCH₃, COOCH₃, NO₂, NH₂
R⁹=F, Cl, Br, CN, OH, OCH₃, COOCH₃, NO₂, NH₂

R²=R³=OCH₃, R⁴=H
R²=R⁴=OCH₃, R³=H
R²=R³=R⁴=OCH₃
R²=R³=H, R⁴=OCH₃
R²=R⁴=OCH₃, R³=OH
R²=R⁴=H, R³=OH
R⁸=F, Cl, Br, CN, OH, OCH₃, COOCH₃, NO₂, NH₂
R⁹=F, Cl, Br, CN, OH, OCH₃, COOCH₃, NO₂, NH₂

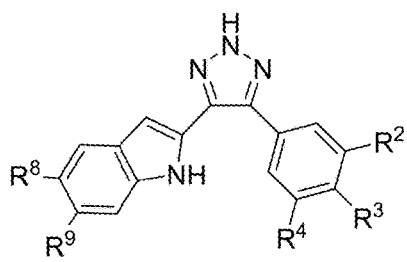

R²=R³=OCH₃, R⁴=H
R²=R⁴=OCH₃, R³=H
R²=R³=R⁴=OCH₃
R²=R⁴=H, R³=OCH₃
R²=R⁴=OCH₃, R³=OH
R²=R⁴=H, R³=OH
R⁸=F, Cl, Br, CN, OH, OCH₃, COOCH₃, NO₂, NH₂
R⁹=F, Cl, Br, CN, OH, OCH₃, COOCH₃, NO₂, NH₂

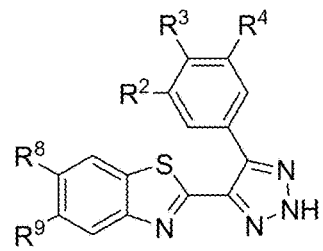

R²=R³=OCH₃, R⁴=H
R²=R³=OCH₃, R⁴=H
R²=R³=R⁴=OCH₃
R²=R⁴=H, R³=OCH₃
R³=R⁴=OCH₃, R³=OH
R²=R⁴=H, R³=OH
R⁸=F, Cl, Br, CN, OH, OCH₃, COOCH₃, NO₂, NH₂
R⁹=F, Cl, Br, CN, OH, OCH₃, COOCH₃, NO₂, NH₂

FIG. 4

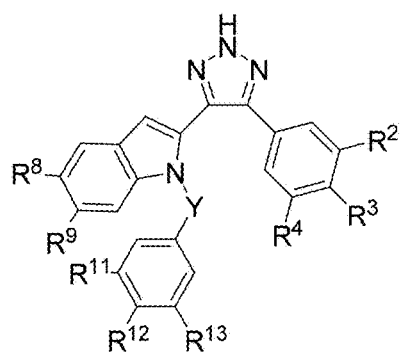
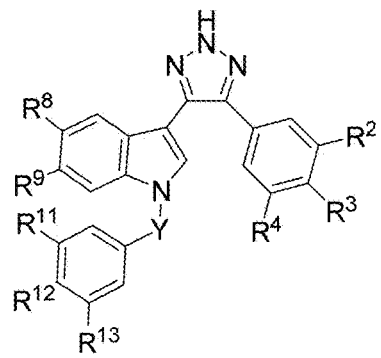

Y=CH$_2$, CO, SO$_2$

R$^2$=R$^3$=OCH$_3$, R$^4$=H
R$^2$=R$^4$=OCH$_3$, R$^3$=H
R$^2$=R$^3$=R$^4$=OCH$_3$
R$^2$=R$^4$=H, R$^3$=OCH$_3$
R$^2$=R$^4$=OCH$_3$, R$^3$=OH
R$^2$=R$^4$=H, R$^3$=OH

R$^8$=H, CH$_3$, CN, CF$_3$, COOH, COOCH$_3$, F, Cl, Br, I, NH$_2$
R$^9$=H, CH$_3$, CN, CF$_3$, COOH, COOCH$_3$, F, Cl, Br, I, NH$_2$
R$^{11}$=H, CH$_3$, CN, CF$_3$, COOH, COOCH$_3$, F, Cl, Br, I, NH$_2$
R$^{12}$=H, CH$_3$, CN, CF$_3$, COOH, COOCH$_3$, F, Cl, Br, I, NH$_2$
R$^{13}$=H, CH$_3$, CN, CF$_3$, COOH, COOCH$_3$, F, Cl, Br, I, NH$_2$

FIG. 5

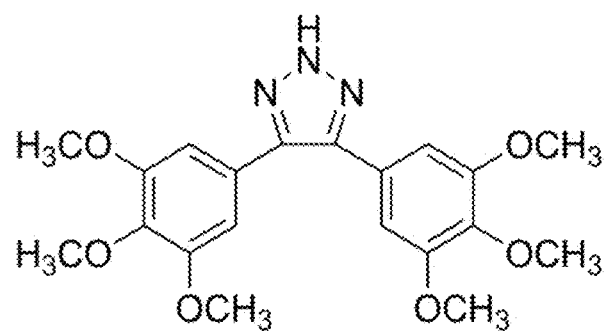
(I)(i)
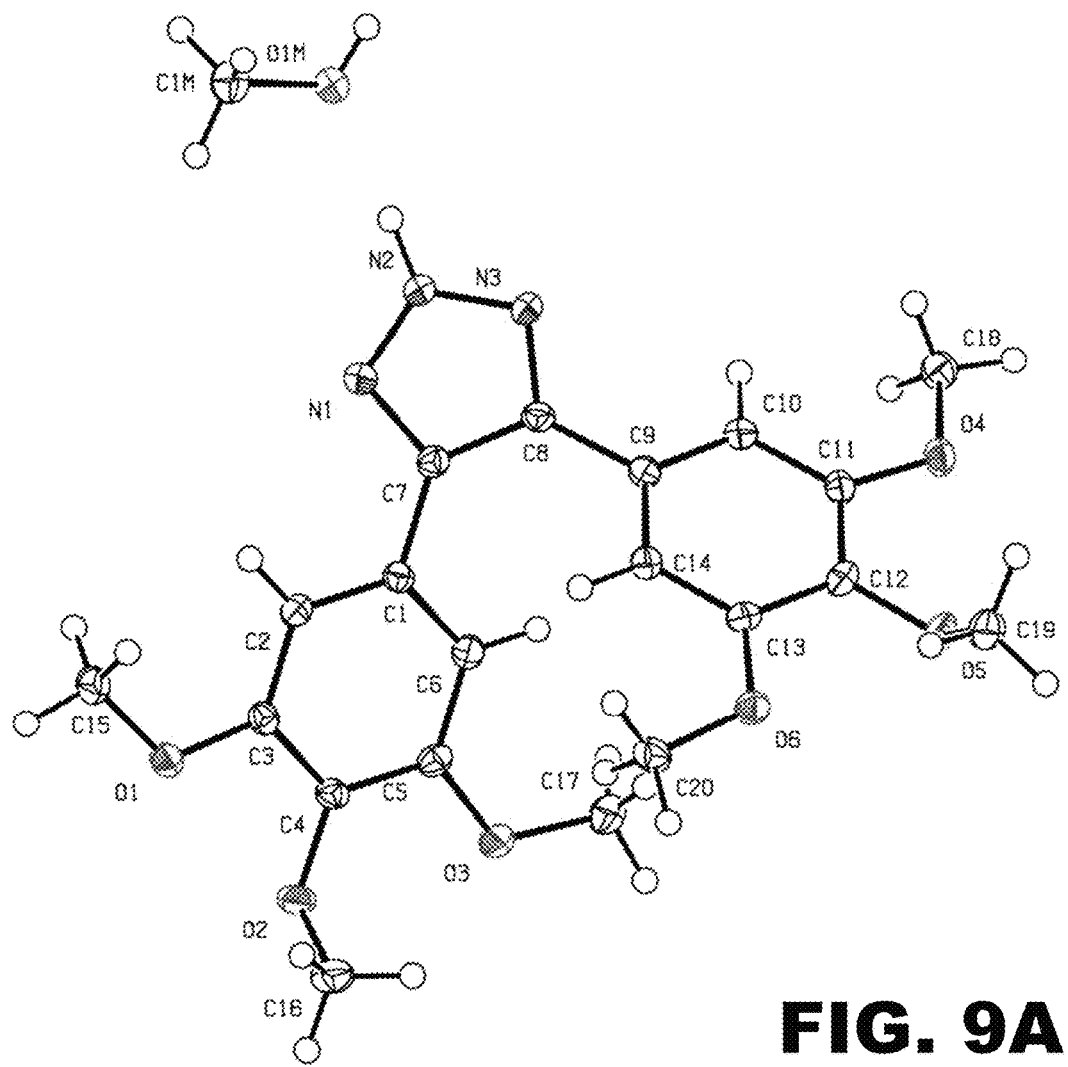
FIG. 9A

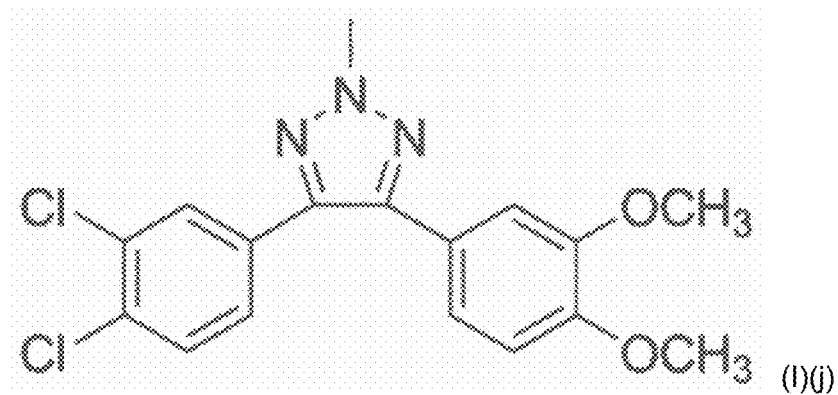
(I)(j)
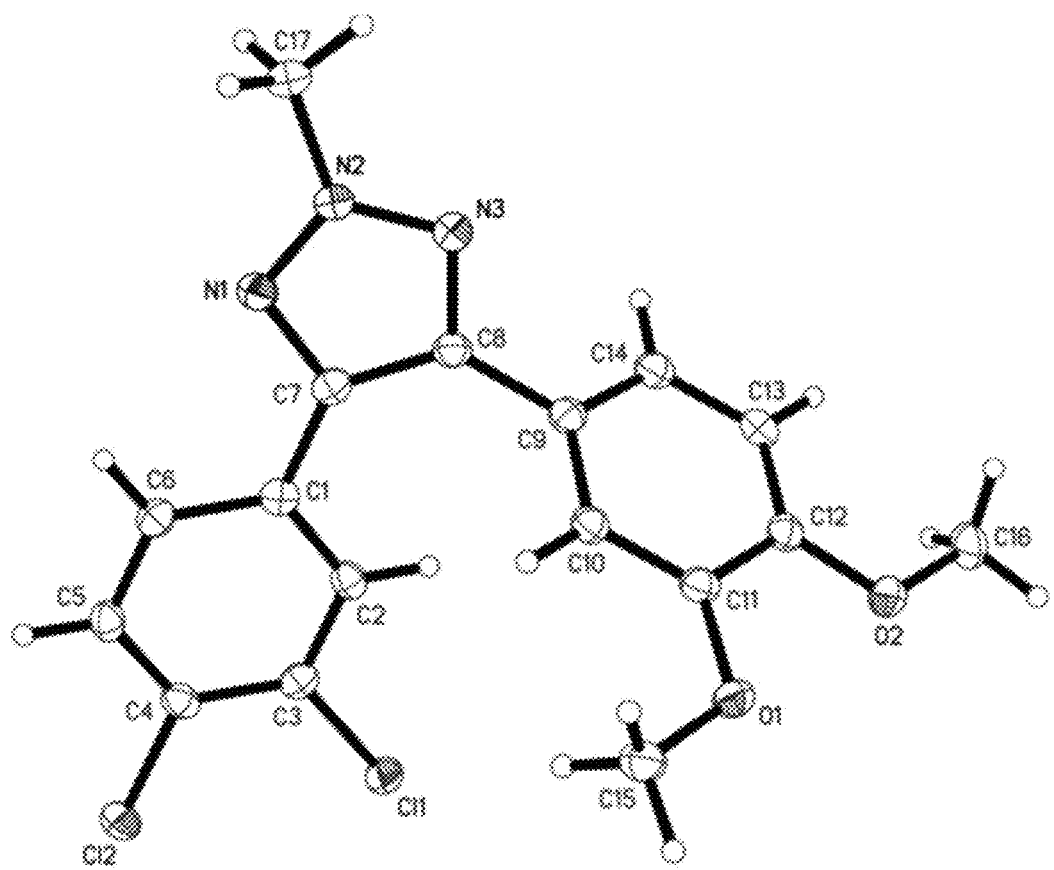
FIG. 9C

DISUBSTITUTED TRIAZOLE ANALOGS

CROSS REFERENCE TO RELATED APPLICATIONS

This application is a continuation-in part of PCT Application PCT/US2015/023628, filed Mar. 31, 2015, which claims the benefit of U.S. provisional application No. 61/972,938, filed Mar. 31, 2014, each of the disclosures of which is hereby incorporated by reference in its entirety.

FIELD OF THE INVENTION

The present invention relates novel disubstituted triazole compositions, their synthesis, and their use as anti-cancer compounds.

BACKGROUND OF THE INVENTION

A total of seventeen combretastatin compounds have been isolated from the South African bushwillow tree *Combretum caffrum* by Pettit and co-workers. Among these seventeen compounds, Combretastatin A4 (CA4) (1) has emerged as the most potent anti-cancer agent. CA4 is a vascular disruptive agent which inhibits tubulin polymerization. CA4 can induce cancer cell cytotoxicity in the low nanomolar range and is also active against multidrug resistant cancer cells. The cis-isomer of CA4 is the biologically active form, but it is known to easily isomerize to its inactive trans-geometrical isomer.

In order to stabilize the active geometrical cis-isomeric form of CA4, various cis-constricted combretastatin analogs have been previously synthesized and tested for their anti-cancer activity. However, in this respect, 4,5-disubstituted-2H-1,2,3-triazoles have received little attention, probably because of the difficulty in preparing them.

In the current work, we have developed a simple and novel synthetic procedure for the synthesis of cis-geometrically configured 4,5-disubstituted-2H,-1,2,4-triazoles as analogs of CA4. The synthesized 4,5-disubstituted-2H,1,2,3-triazoles have been evaluated for their anticancer activity and are found to be potent cytotoxic agents.

SUMMARY OF THE INVENTION

Among the various aspects of the present disclosure is a compound comprising Formula (I):

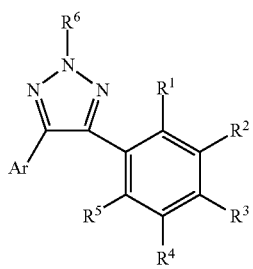

wherein:
$R^1$, $R^2$, $R^3$, $R^4$, $R^5$ and $R^6$ are independently chosen from hydrogen, hydrocarbyl, substituted hydrocarbyl, alkylalkylamino, amidine, amino, carboxyl, cyano, ester, halogen, hydroxyl, and nitro; and
Ar is an aryl or substituted aryl group.

In another aspect, the present disclosure provides pharmaceutical composition comprising Formula (I) and at least one pharmaceutically acceptable excipient.

In yet a further aspect, the disclosure provides a method of making the compound comprising Formula (I). The method comprises contacting a compound comprising Formula (II) or Formula (III) with an azide,

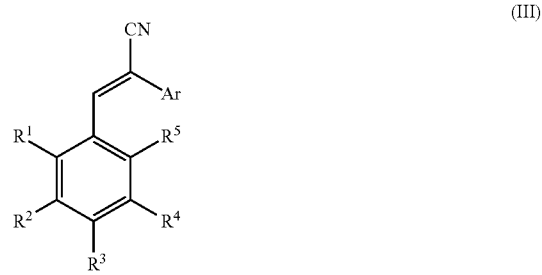

wherein $R^1$, $R^2$, $R^3$, $R^4$, $R^5$, and Ar are as defined above.

In still another embodiment, the present disclosure provides a method of inhibiting tubulin polymerization, the method comprises administering a compound comprising Formula (I) to a subject.

Other features and iterations of the disclosure are provided in more detail herein.

BRIEF DESCRIPTION OF THE DRAWINGS

The patent or application file contains at least one drawing executed in color. Copies of this patent or patent application with color drawing(s) will be provided by the Office by request and payment of the necessary fee.

FIG. 1 shows combretastatin A4 (1) and various cis-constrained 4,5-disubstituted-2H-1,2,3-triazole analogs (3-8).

FIG. 2 shows examples of compounds of Formula (I).

FIG. 4 shows benzothiophen-2-yl, benzofuran-2-yl, indole-2-yl and benzthiozole combretastatin 2H, 1,2,3-triazoles.

FIG. 5 shows N-alkyl indole combretastatin 2H-1,2,3-triazoles.

FIG. 9A, FIG. 9B and FIG. 9C show X-ray crystallographic studies of compounds comprising Formula (I), specifically (FIG. 9A) a compound of Formula (I)(i), (FIG. 9B) a compound of Formula (I)(f), and (FIG. 9C) a compound of Formula (I)(j).

FIG. 11A depicts the experimental design. FIG. 11B depicts a graph showing the average radiance following treatment with Compound 8 and control. FIG. 11C depicts images showing the intensity of GFP expressing cells following treatment with Compound 8 and control.

DETAILED DESCRIPTION OF THE INVENTION

Figure 3:
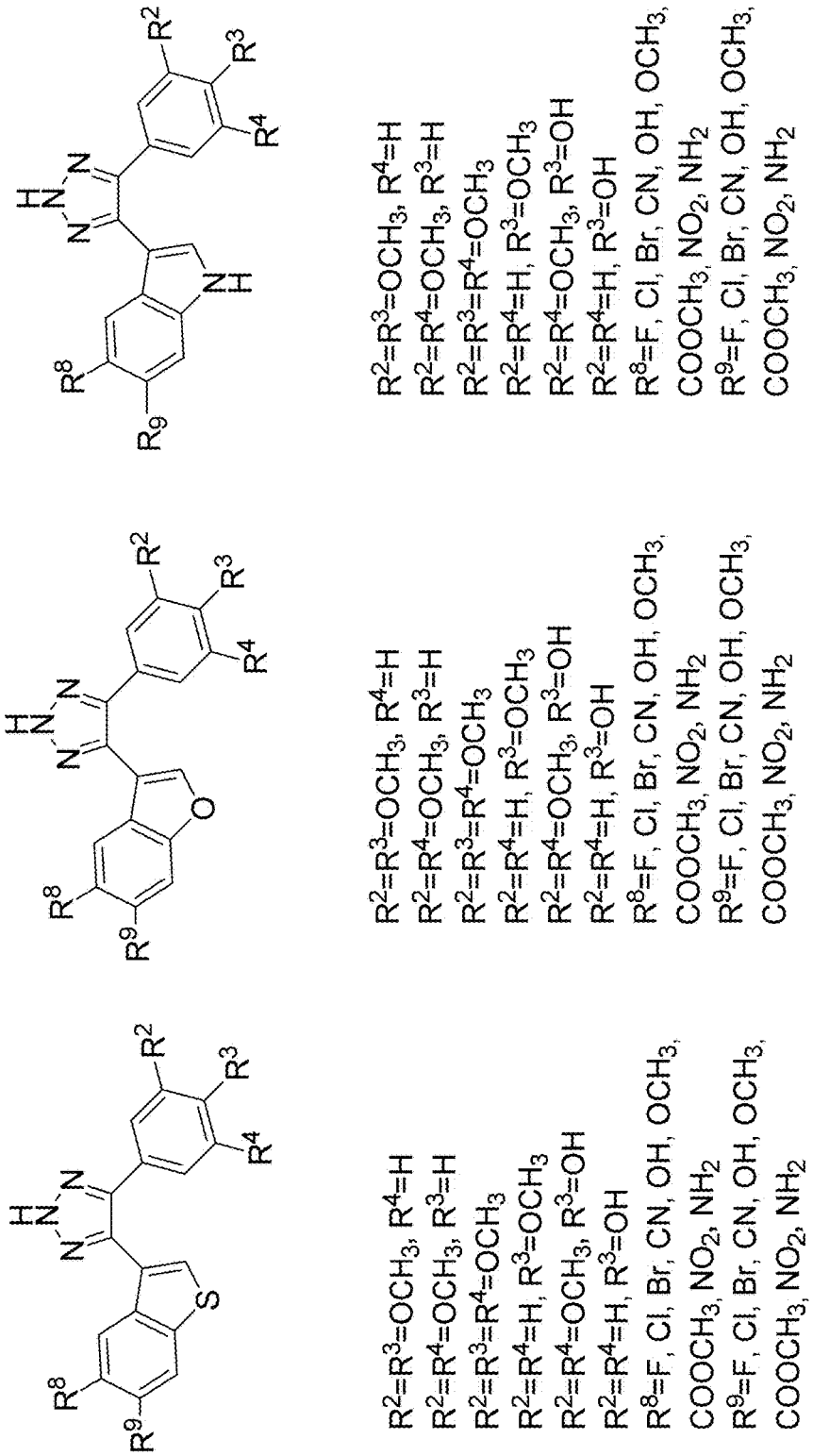
FIG. 3 shows benzothiophen-3-yl, benzofuran-3-yl and indole-3-yl combretastatin 2H, 1,2,3-triazoles.

Briefly, the present invention relates to disubstituted triazole analogs. The analogs generally have a triazole structural feature substituted with both a stilbene (or combretastatin) structural feature and another aryl structural feature, each of which may each be further derivatized. These analogs show novel and unexpected properties in terms of biological activity, and in particular showing cytotoxicity against various cancer cell lines. It is thought that this cytotoxicity is due to the ability of the compound to bind to tubulin and to inhibit tubulin polymerization. Due to this activity, the compounds described herein may be active in the treatment of a variety of diseases including in the treatment of cancer.

I. Compositions (a) Compound Comprising Formula (I)

One aspect of the invention provides compounds comprising Formula (I):

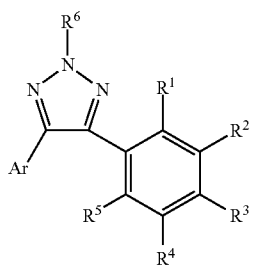

(I)

wherein:

$R^1$, $R^2$, $R^3$, $R^4$, $R^5$ and $R^6$ are independently chosen from hydrogen, hydrocarbyl, substituted hydrocarbyl, alkylalkylamino, amidine, amino, carboxyl, cyano, ester, halogen, hydroxyl, and nitro; and Ar is an aryl or substituted aryl group.

$R^1$, $R^2$, $R^3$, $R^4$, $R^5$ and $R^6$ are independently chosen from hydrogen, hydrocarbyl, substituted hydrocarbyl, alkylalkylamino, amidine, amino, carboxyl, cyano, ester, halogen, hydroxyl, and nitro. Alkylalkylamino groups are disubstituted amine groups. Each of the alkyl groups may be the same or different. In one embodiment, both alkyl groups are lower alkyl groups. The amidine nitrogen groups may be further substituted by hydrogen, hydrocarbyl, or substituted hydrocarbyl at each position. Preferably, the amidine nitrogens are each substituted by hydrogen. Where the group is an amine, the amine may be a primary, secondary, or tertiary amine. Preferably, amine substituents are lower alkyl groups. Ester groups may be attached to the phenyl ring at either the carbonyl end or at the oxygen end of the ester. The opposite terminus may be hydrocarbyl or substituted hydrocarbyl, and is preferably a lower alkyl. Aryl groups include, but are not limited to, phenyl, benzyl, substituted benzyl, benzoyl, substituted benzoyl, naphthyl, substituted naphthyl, naphthoyl, substituted naphthoyl, benzenesulphonyl, substituted benzenesulphonyl, heteroaryl, substituted heteroaryl, aroyl, and heteroaroyl.

Non-limiting examples of aryl substituents are shown below:

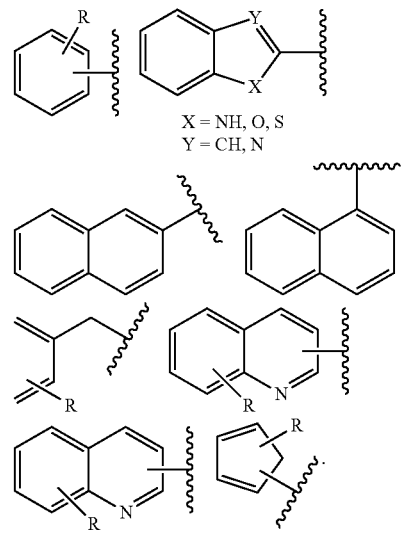

X = NH, O, S
Y = CH, N

In one embodiment, $R^2$, $R^3$, and $R^4$ are independently chosen from hydrogen, methoxy, ethoxy, benzyloxy, substituted benzyloxy, hydroxyl, and lower alkyl groups. In another embodiment, $R^1$, $R^2$, $R^3$, $R^4$ and $R^5$ are chosen from hydrogen, hydroxyl, and alkoxy. In a preferred embodiment, $R^1$ and $R^5$ are both hydrogen. In still another preferred embodiment, $R^1$, $R^5$, and $R^6$ are hydrogen.

In certain embodiments, $R^2$, $R^3$, and $R^4$ are chosen from hydrogen, hydroxyl, and alkoxy. In one preferred embodiment, $R^2$ and $R^4$ are methoxy and $R^1$, $R^3$, and $R^5$ are hydrogen. In another preferred embodiment, $R^2$, $R^3$, and $R^4$ are methoxy and $R^1$ and $R^5$ are hydrogen. In still another preferred embodiment, $R^2$ is hydroxyl, $R^3$ is methoxy, and $R^1$, $R^4$ and $R^5$ are hydrogen.

In some embodiments, $R^6$ is chosen from hydrogen, alkyl including $C_1$-$C_6$ alkyl groups, aryl, acyl, aroyl, heteroaryl, heteroaroyl, and benzyl. In a preferred embodiment, $R^6$ is hydrogen. In yet another preferred embodiment $R^6$ is methyl.

Aryl, as used herein, refers to a substituent derived from any aromatic (including heteroaromatic) ring. Aromatic rings include phenyl, napthyl, thienyl, imidazole, oxazole, thiophene and the like. The aryl group may be substituted or unsubstituted and substitutions may be at any open site on the aryl group. When substituted, the substitutions are chosen from hydrocarbyl, substituted hydrocarbyl, alkylalkylamino, amidine, amino, carboxyl, cyano, ester, halogen, hydroxyl, nitro, and $CF_3$. Alkylalkylamino groups are disubstituted amine groups. Each of the alkyl groups may be the same or different. In one embodiment, both alkyl groups are lower alkyl groups. The amidine nitrogen groups may be further substituted by hydrogen, hydrocarbyl, or substituted hydrocarbyl at each position. Preferably, the amidine nitrogens are each substituted by hydrogen. Where the group is an amine, the amine may be a primary, secondary, or tertiary amine. Preferably, amine substituents are lower alkyl groups. Ester groups may be attached to the phenyl ring at either the carbonyl end or at the oxygen end of the ester. The opposite terminus may be hydrocarbyl or substituted hydrocarbyl, and is preferably a lower alkyl. Preferred substituents include, but are not limited to, halogens hydroxyl and alkoxy, and especially methoxy.

The compound comprising Formula (I) may be a free form or a salt. When the compound is in a salt form, the salt is preferably a pharmaceutically acceptable salt. Pharmaceutically acceptable salts may include, without limitation, hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpropionate, isobutyrate, hypophosphite, maleic, malic, citrate, isocitrate, succinate, lactate, gluconate, glucuronate, pyruvate, oxalate, fumarate, propionate, aspartate, glutamate, benzoate, terephthalate, and the like. In other embodiments, the pharmaceutically acceptable salt includes an alkaline or alkaline earth metal ion salt. In particular, sodium, potassium or other pharmaceutically acceptable inorganic salts are used. The salt forms may be amorphous or in various polymeric forms including hydrates, or solvates with alcohols or other solvents.

In one embodiment, the disclosure provides a compound comprising Formula (I)(a):

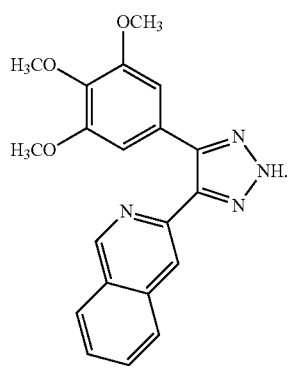

(I)(a)

In still another embodiment, the disclosure provides a compound comprising Formula (I)(b):

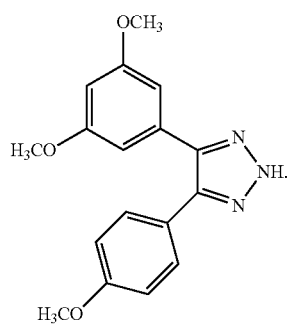

(I)(b)

In still another embodiment, the disclosure provides a compound comprising Formula (I)(c):

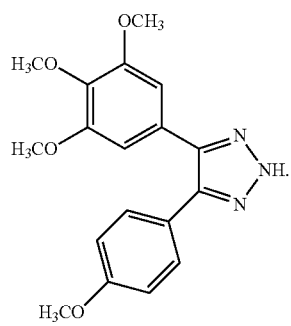

(I)(c)

In still a further embodiment, the disclosure provides a compound comprising Formula (I)(d):

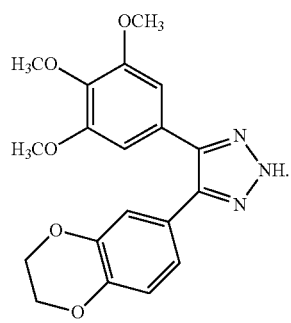

(I)(d)

In still a further embodiment, the disclosure provides a compound comprising Formula (I)(e):

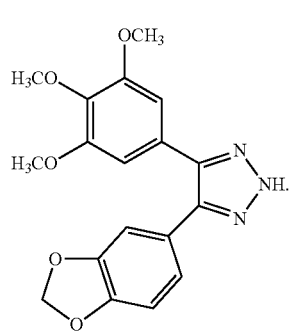

(I)(e)

In still a further embodiment, the disclosure provides a compound comprising Formula (I)(f):

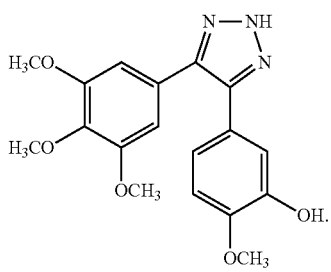

Additional embodiments are shown in the below table, figures and examples.

TABLE 1

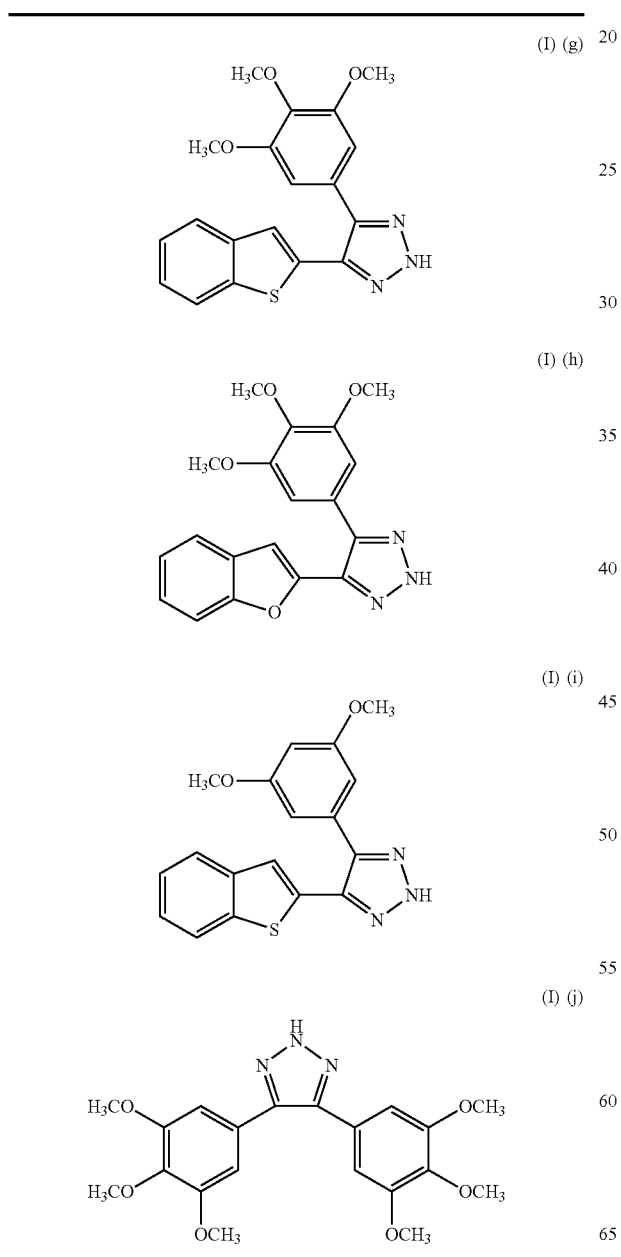

TABLE 1-continued

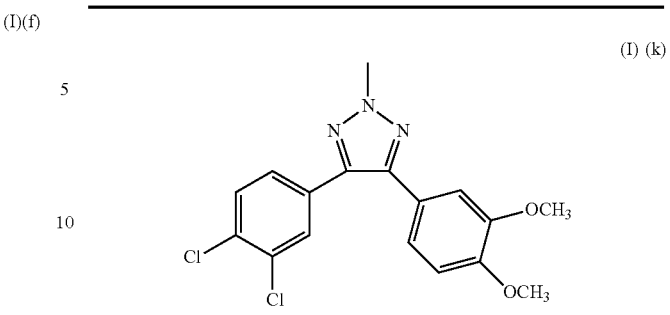

(b) Pharmaceutical Compositions

The disclosure also provides a pharmaceutical composition comprising a compound comprising Formula (I) and at least one pharmaceutically acceptable excipient. In various embodiments, one or more of the compounds described in section (I) may be combined with at least one pharmaceutically acceptable excipient.

(i) Excipient

A pharmaceutical composition of the disclosure comprises at least one pharmaceutically acceptable excipient. Non-limiting examples of suitable excipients may include diluents, binders, fillers, buffering agents, pH modifying agents, disintegrants, dispersing agents, stabilizers, preservatives, and coloring agents. The amount and types of excipients may be selected according to known principles of pharmaceutical science.

In one embodiment, the excipient may include at least one diluent. Non-limiting examples of suitable diluents may include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose.

In another embodiment, the excipient may comprise a binder. Suitable binders may include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers may include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Buffers may include phosphates, carbonates, citrates, and the like. Representative examples of suitable buffering agents may include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be sodium carbonate or sodium bicarbonate.

In another alternate embodiment, the excipient may also include a preservative. Non-limiting examples of suitable preservatives may include antioxidants, such as alpha-tocopherol or ascorbate, or EDTA (ethylenediaminetetraacetic acid), EGTA (ethylene glycol tetraacetic acid), BHA (butylated hydroxyanisole), BHT (butylated hydroxytoluene), and the like.

In a further embodiment, the excipient may include a disintegrant. Suitable disintegrants may include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and micro-crystalline cellulose.

In a further embodiment, the excipient may include a lubricant. Non-limiting examples of suitable lubricants may include minerals such as talc or silica; and fats such as vegetable stearin, magnesium stearate, or stearic acid.

In still another embodiment, it may be desirable to provide a coloring agent. Suitable color additives may include, but are not limited to, food, drug and cosmetic colors (FD&C), drug and cosmetic colors (D&C), or external drug and cosmetic colors (Ext. D&C).

The weight fraction of the excipient(s) in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The pharmaceutical composition may be mixed with one or more excipients to form a solid, liquid, or cream dosage form. Methods of formulating a solid, liquid, or cream dosage form are known in the art.

(ii) Optional Additional Pharmaceutical Ingredient

Optionally, the compound comprising Formula (I) may be combined with other compounds comprising Formula (I) or may be combined with one or more than one additional active pharmaceutical ingredients.

II. Method for Synthesis (a) Method for Producing a Compound Comprising Formula (I)

In another embodiment, the disclosure provides a method of making the compound comprising Formula (I). The method comprises contacting a compound comprising Formula (II) or Formula (III) with an azide. The compound of Formula (II) and Formula (III) comprises:

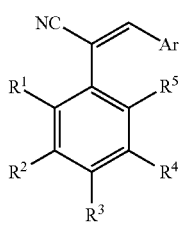

(II)

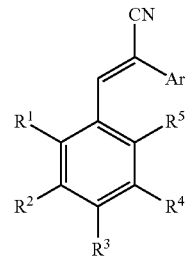

(III)

wherein, $R^1$, $R^2$, $R^3$, $R^4$, $R^5$ and Ar may be chosen as described in section (I).

The compound comprising Formula (II) or Formula (III) is contacted with an azide. As used herein, an azide, is any molecule with an azide ($N_3$—) functional group. Without limitation, the azide may be chosen from trialkylsilyl azide, mesyl and tosyl azides, alkyl azides, aryl azides, sulfonyl azides, alkaline metal azides, aluminum azide, and combinations thereof.

The mole to mole ratio of the compound comprising Formula (II) or Formula (III) to the azide can range over different embodiments of the invention. In one embodiment, the ratio of the compound comprising Formula (II) or Formula (III) to the azide varies from about 0.9:1 to about 1:10. In some embodiments, the mole to mole ratio of the compound comprising Formula (II) or Formula (III) to the azide is about 1:1 to about 1:15. In various embodiments, the mole to mole ratio of the compound comprising Formula (II) or Formula (III) to the azide is about 1:1, about 1:2, about 1:3, about 1:4, about 1:5, or about 1:6, about 1:7, about 1:8, about 1:9, or about 1:10. In an exemplary embodiment, the mole to mole ratio of the compound comprising Formula (II) or Formula (III) to the azide is 1:3.

The contacting of the compound comprising Formula (II) or Formula (III) and the azide occurs in the presence of a proton acceptor or a proton donor. In one embodiment, the contacting of the compound comprising Formula (II) or Formula (III) and the azide occurs in the presence of a proton acceptor. In another embodiment, the contacting of the compound comprising Formula (II) or Formula (III) and the azide occurs in the presence of a proton donor. Suitable proton acceptors include, but are not limited to borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), ammonia and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. Suitable proton donors include, but are not limited to acetic acid, formic acid, trichloroacetic, hydrofluoric, hydroiodic acid, hydrobromic acid, hydrochloric acid, perchloric acid, sulfuric acid, p-toluenesulfonic acid, methanesulfonic acid, fluorosulfuric acid, and triflic acid. In one preferred embodiment, the contacting of the compound comprising Formula (II) or Formula (III) and the azide is conducted in the presence of aqueous hydrochloric acid. In another embodiment, the contacting of the compound comprising Formula (II) or Formula (III) and the azide is conducted in the presence of aqueous ammonium chloride.

In some embodiments, the compound comprising Formula (II) or (III) is reacted in the presence of a Lewis base. Suitable Lewis bases include, but are not limited to L-proline, pyrrolidine, DMAP, DIPEA, Na-t-Bu, glycine, $P(OMe)_3$, imidazole, $Ti(OiPr)_4$, and HMPA. In some embodiments, the compound comprising Formula (II) or (III) is reacted in the presence of $NH_4Cl$, KCl, $NH_4Br$ or varying salts thereof.

The amount of the proton donor or acceptor which is added may vary. Generally, the proton acceptor is added in excess to the compound comprising Formula (II) or Formula (III). In some embodiments, the mole to mole ratio of the compound comprising Formula (II) or Formula (III) to the proton acceptor or donor can range from about 1:1.1 to about 1:25. In some embodiments, the mole to mole ratio of the compound comprising Formula (II) or Formula (III) to the proton acceptor or donor is about 1:1, about 1:2, about 1:3, about 1:4, about 1:5, or higher.

The reaction is preferably carried out in a solvent. The solvent may be chosen without limitation from including alkane and substituted alkane solvents (including cycloalkanes) alcohol solvents, halogenated solvents, aromatic hydrocarbons, esters, ethers, ketones, and combinations thereof. Non-limiting examples of suitable organic solvents are acetonitrile, acetone, allyl alcohol, benzene, butyl acetate, carbocyclic solvents, chlorobenzene, chloroform, chloromethane, cyclohexane, cyclopentane, dichloromethane (DCM), dichloroethane, diethyl ether, dimethoxyethane (DME), dimethylformamide (DMF), dimethyl sulfoxide (DMSO), dioxane, ethanol, ethyl acetate, ethylene dichloride, ethylene bromide, formic acid, fluorobenzene, heptane, hexane, isobutylmethylketone, isopropanol, isopropyl acetate, N-methylpyrrolidone, methanol, methylene bromide, methylene chloride, methyl iodide, methylethylketone, methyltetrahydrofuran, pentyl acetate, propanol, n-propyl acetate, sulfolane, tetrahydrofuran (THF), tetrachloroethane, toluene, trichloroethane, water, xylene and combinations thereof. In one preferred embodiment, the solvent is selected from water, alcohols, DMF, DMSO, benzene, toluene, xylenes or combinations thereof.

In one preferred embodiment, the solvent is a mixture of DMF and water. The ratio of DMF to water in volumetric proportions may range from about 0.5:1 to about 1:10. In some embodiments, the ratio of DMF to water is about 1:1, about 1:2, about 1:3, about 1:4, about 1:5, about 1:6, about 1:7, about 1:8, about 1:9, or about 1:10. In one preferred embodiment, the volumetric ratio of DMF to water is about 1:4.

The amount of time over which the reaction between the azide and the compound comprising Formula (II) or Formula (III) is conducted may also vary within different embodiments. In some embodiments, the reaction may be conducted over a period of about 1 hour to about 36 hours. In particular embodiments, the reaction is carried out for about 6 hours, about 8 hours, about 10 hours, about 12 hours, about 14 hours, about 16 hours, about 18 hours, about 20 hours, about 22 hours, about 24 hours, about 26 hours, about 28 hours, about 30 hours, about 32 hours, about 34 hours, or about 36 hours.

The temperature of the reaction between the compound comprising Formula (II) or Formula (III) and the azide may vary over different embodiments, in some embodiments the temperature may range from about 50° C. to about 150° C. In particular embodiments, the temperature may range from about 110° C. to about 120° C., from about 115° C. to about 120° C., from about 120° C. to about 130° C., from about 125° C. to about 135° C., from about 130° C. to about 135° C., from about 130° C. to about 140° C., or from about 135° C. to about 140° C.

Reaction completion may be monitored by thin layer chromatography or any other acceptable measurement. A complete reaction, as used herein, means that the compound comprising Formula (II) or Formula (III) is substantially depleted, while the compound comprising Formula (I) is present in increased amounts. Once the reaction is complete, the reaction mixture is generally cooled to a temperature ranging from 15° C. to about 40° C. A proton donor and water is generally added after reaction completion. The proton donor and water may be added slowly and stirred over the course of several minutes to an hour or until precipitation of a solid occurs. Preferably, the hydrochloric acid is added to the complete reaction and stirred for 10-30 minutes.

The yield of the disubstituted triazole can vary from about 40% yield to about 90% yield. In some embodiments, the yield is above 40%, above 50%, above 60%, above 70%, above 80%, above 90% or higher.

The synthesized compounds may be used in their crude form or they may be purified. The compounds may be purified by any suitable method known in the art including through column chromatography, crystallization, distillation, filtration, extraction, and the like. In one preferred embodiment, the compounds are recrystallized from a solvent.

III. Methods of Use

In still another aspect, the present disclosure provides a method of inhibiting tubulin polymerization in a subject. The method comprises administering a compound comprising Formula (I) to a subject.

Without being bound to any theory, compounds comprising Formula (I) are thought to bind to tubulin. The binding at this site is thought to inhibit tubulin polymerization, and in turn, inhibit formation of vasculature. In tumors, a developing vasculature is key to tumor growth and migration. Accordingly, inhibition of tubulin polymerization is important to the treatment of various disease states.

In another embodiment, a method for treating cancer is provided. The method comprises administering a compound comprising Formula (I) to a subject. In still another embodiment, a method for reducing tumor size is provided. Cancers or tumors treatable by the method may include, without limitation, prostate cancer, ovarian cancer, breast cancer, brain cancer, hepatic cancer, leukemia, lung cancer, colon cancer, CNS cancer, melanoma, renal cancer, pancreatic cancer, gastric cancer, lymphoma and the like.

The compounds may be administered to the subject by a variety of routes. For example, a compound comprising Formula (I) may be administered orally via a solid or liquid dosage form (tablet, gel cap, time release capsule powder, solution, or suspension in aqueous or non-aqueous liquid), parenterally (i.e., subcutaneously, intradermally, intravenously, (i.e., as a solution, suspension or emulsion in a carrier), intramuscularly, intracranially, or intraperitoneally), or topically (i.e., transdermally or transmucosally, including, but not limited to buccal, rectal, vaginal and sublingual). In one embodiment, the compounds may be administered in saline or with a pharmaceutically acceptable excipient as described in section (I). The compound may be administered as primary therapy, or as adjunct therapy, either following local intervention (surgery, radiation, local chemotherapy) or in conjunction with at least one other chemotherapeutic agent.

Suitable subjects may include, without limit, humans, as well as companion animals such as cats, dogs, rodents, and horses; research animals such as rabbits, sheep, pigs, dogs, primates, mice, rats and other rodents; agricultural animals such as cows, cattle, pigs, goats, sheep, horses, deer, chickens and other fowl; zoo animals; and primates such as chimpanzees, monkeys, and gorillas. The subject can be of any age without limitation. In a preferred embodiment, the subject may be a human.

Generally, the compound comprising Formula (I) will be administered in a therapeutically effective amount which includes prophylactic amounts or lower dosages for example, when combined with another agent. As used herein, "an effective amount" refers to doses of compound sufficient to provide circulating concentrations high enough to impart a beneficial effect on the recipient thereof. The precise amount to be administered can be determined by the skilled practitioner in view of desired dosages, side effects, and medical history of the patient.

The compounds comprising Formula (I) may also be characterized by their cytotoxic effects when contacted with cells. In some embodiments, the compounds inhibit the growth of a cell. In other embodiments, the compounds kill cells. Accordingly, the compounds of the present invention may be characterized by $GI_{50}$ values and $LC_{50}$ values. $GI_{50}$ refers to the molar drug concentration required to cause 50% growth inhibition compared to an untreated cell. $LC_{50}$ refers to the concentration required to kill 50% of cells. In still another embodiment, the disclosure provides a method for inhibiting growth of a cell by contacting the cells with a compound comprising Formula (I), and in a still further embodiment, the disclosure provides a method for killing cells by contacting the cells with a compound comprising Formula (I). Cells may be chosen from, without limitation, those listed in TABLE 2.

In some embodiments, the compounds comprising Formula (I) have an $LC_{50}$ of less than about 100 µM, or less than 80 µM, or less than about 60 µM, or less than about 40 µM, or less than about 20 µM, or less than about 1 µM. In other embodiments, the compounds comprising Formula (I) have a $GI_{50}$ of less than about 100 µM, or less than 80 µM, or less than about 60 µM, or less than about 40 µM, or less than about 20 µM, or less than about 1 µM.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein refers to straight or branched chain alkyl groups having in the range of about 1 to about 10 carbon atoms. A substituted alkyl group has one or more heteroatom substituents as described in the definition of substituted hydrocarbyl.

The term "alkylaryl" refers to alkyl substituted aryl groups, and "substituted alkylaryl refers to alkylaryl groups further bearing one or more substitutents.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl, or substituted naphthyl.

The term "arylalkynyl" refers to aryl-substituted alkynyl groups and "substituted arylalkynyl" refers to arylalkynyl groups further bearing one or more substituents.

The term "aroyl" refers to aryl-substituted species such as benzoyl and "substituted aroyl" refers to aroyl moieties further bearing one or more substituents as set forth above.

The term "cycloalkyl" refers to cyclic ring-containing moieties containing in the range of about 3 up to 7 carbon atoms and "substituted cycloalkyl" refers to cycloalkyl moieties further bearing one or more substituents.

The terms "halide" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and having in the range of 2 up to 12 carbon atoms, or preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thiol.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbamate, carbocyclo, cyano, ester, ether, halogen, heterocyclo, hydroxyl, keto, ketal, phospho, nitro, thio, trifluoromethyl, sulfonyl, sulfonamide, and the like.

EXAMPLES

Example 1: Biological Evaluation at the NCI, In Vitro Growth Inhibition and Cytotoxicity All synthesized compounds were submitted and evaluated for their anticancer activity at the National Cancer Institute (NCI). The submitted compounds were tested against a panel of 60 different human cancer cell lines, initially at a single concentration of 10 μM. Compounds showing the best growth inhibition activity were then selected for a complete five-dose response study. The anti-tumor effect of each compound was then determined by its $GI_{50}$ and $LC_{50}$ values. The $GI_{50}$ and $LC_{50}$ values of the 5 most potent compounds (FIG. 1) against the panel of 60 human cancer cell lines are given in TABLE 2.

TABLE 2

Growth inhibition activity of examples 3, 4, 5, 6 and 7

| Panel/cell line | Example 3 (I)(a) | | Example 4 (I)(b) | | Example 5 (I)(c) | | Example 6 (I)(d) | | Example 7 (I)(e) | |
| --- | --- | --- | --- | --- | --- | --- | --- | --- | --- | --- |
| | $GI_{50}$ (nM) | TGI (μM) | $GI_{50}$ (nM) | TGI (μM) | $GI_{50}$ (nM) | TGI (μM) | $GI_{50}$ (nM) | TGI (μM) | $GI_{50}$ (nM) | TGI (μM) |
| Leukemia | | | | | | | | | | |
| CCRF-CEM | 37.3 | >100 | 31.9 | 21.8 | <10 | 46.3 | 33.7 | >100 | 282 | >100 |
| HL-60(T13) | 30.0 | 5.74 | 22.7 | NA | <10 | NA | 18.9 | 0.08 | 201 | NA |
| K-562 | 25.7 | >100 | <10 | >100 | <10 | >100 | <10 | >100 | 49.6 | >100 |
| MOLT-4 | 68.2 | >100 | 48.2 | 20.0 | 12.0 | 16.1 | 39.9 | 11.6 | 572 | 51.8 |
| RPMI-8226 | 36.5 | 87.6 | 36.8 | 21.1 | <10 | 24.6 | 32.5 | 11.0 | 326 | 22.1 |
| SR | 21.1 | >100 | <10 | 16.9 | <10 | >100 | <10 | 24.0 | 43.6 | 11.6 |
| Non-Small Cell Lung Cancer | | | | | | | | | | |
| A549/ATCC | 54.1 | >100 | 37.4 | >100 | <10 | 73.4 | 22.9 | 22.6 | 289 | 50.9 |
| HOP-62 | 46.7 | >100 | 25.0 | >100 | <10 | 72.4 | 18.2 | 19.3 | 336 | >100 |
| HOP-92 | 98.9 | 11.3 | <10 | 2.67 | <10 | 0.08 | <10 | 0.54 | 122 | 1.59 |
| NCI-H23 | 64.9 | >100 | 37.7 | 27.9 | <10 | 68.7 | 48.0 | 41.7 | 767 | >100 |
| NCI-H460 | 38.1 | >100 | 34.2 | >100 | <10 | 10.9 | 24.6 | 20.0 | 335 | 28.7 |
| Colon Cancer | | | | | | | | | | |
| COLO 205 | 228 | 1.16 | 149 | 0.64 | 29.2 | 0.12 | 26.7 | 0.07 | 311 | 1.3 |
| HCC-2998 | 230 | >100 | 45.9 | 11.4 | 24.9 | 22.4 | 39.4 | 17.5 | >1000 | 24.6 |
| HCT-116 | 40.2 | NA | <10 | 1.47 | <10 | >100 | <10 | 0.81 | 181 | 15.6 |
| 1-ICT-15 | 37.3 | >100 | <10 | 5.13 | <10 | >100 | <10 | >100 | 125 | >100 |
| HT29 | 214 | 14.5 | 47.6 | 20.5 | <10 | 10.8 | 25.3 | 12.3 | 392 | 12.5 |
| KM12 | 35.3 | >100 | 29.8 | 23.8 | <10 | 0.05 | <10 | 11.2 | 70.0 | 11.9 |
| SW-620 | 40.6 | >100 | 29.5 | >100 | <10 | >100 | <10 | >100 | 105 | >100 |
| CNS Cancer | | | | | | | | | | |
| SF-268 | 503 | >100 | 177 | >100 | <10 | 90 | 68.5 | >100 | >1000 | >100 |
| SF-295 | 14.4 | >100 | 10.8 | 0.15 | <10 | 27.5 | <10 | 42.8 | 98.9 | 3.61 |
| SF-539 | 20.0 | 0.05 | 13.8 | 0.04 | <10 | <0.01 | <10 | NA | 181 | 0.54 |
| SNB-19 | 52.5 | >100 | 36.9 | >100 | <10 | >100 | 29.4 | >100 | 501 | >100 |
| SNB-75 | 15.7 | NA | 14.2 | >100 | <10 | NA | <10 | 21.9 | 82.4 | NA |
| U251 | 37.1 | 46.9 | 37.9 | >100 | <10 | 16.5 | 20.1 | 22.7 | 302 | 11.2 |

TABLE 2-continued

Growth inhibition activity of examples 3, 4, 5, 6 and 7

| Panel/cell line | Example 3 (I)(a) | | Example 4 (I)(b) | | Example 5 (I)(c) | | Example 6 (I)(d) | | Example (I)(e) | |
|---|---|---|---|---|---|---|---|---|---|---|
| | $GI_{50}$ (nM) | TGI (µM) | $GI_{50}$ (nM) | TGI (µM) | $GI_{50}$ (nM) | TGI (µM) | $GI_{50}$ (nM) | TGI (µM) | $GI_{50}$ (nM) | TGI (µM) |
| Melanoma | | | | | | | | | | |
| LOX IMVI | 65.2 | >100 | 75.5 | >100 | <10 | >100 | 17.5 | 37.8 | 545 | 87.1 |
| M14 | 21.5 | NA | <10 | >100 | <10 | 23.0 | <10 | NA | NA | 12.0 |
| MDA-MB-435 | <10 | NA | <10 | 0.01 | <10 | <0.01 | <10 | NA | 94.8 | NA |
| SK-MEL-2 | 26.9 | 4.24 | 55.5 | >100 | <10 | 30.5 | <10 | 18.1 | 23.6 | 55.7 |
| SK-MEL-28 | >1000 | 6.33 | NA | NA | NA | 60.7 | >100 | 34.8 | 244 | 43.5 |
| 5K-MEL-5 | 12.6 | 0.35 | 26.7 | 0.32 | <10 | 0.02 | <10 | 0.16 | >1000 | 11.9 |
| UACC-62 | 157 | 4.61 | <10 | >100 | >1000 | >100 | >100 | 21.2 | >1000 | 30.8 |
| Ovarian Cancer | | | | | | | | | | |
| IGROV1 | 64.8 | >100 | 50.9 | >100 | <10 | 21.5 | 33.2 | 30.3 | >1000 | >100 |
| OVCA R-3 | 10.8 | 0.04 | 24.4 | >100 | <10 | <0.01 | <10 | <0.01 | 432 | 0.37 |
| OVCAR-4 | 77.4 | >100 | NA | >100 | <10 | >100 | 33.6 | 57.2 | 76.3 | >100 |
| NCI/ADR-RES | 23.1 | 66.1 | <10 | 0.08 | <10 | 17.5 | <10 | 69.7 | 84.9 | 24.0 |
| SK-OV-3 | 75.0 | 97.7 | 45.8 | >100 | <10 | 40.3 | <10 | 12.7 | 486 | 93.2 |
| Renal Cancer | | | | | | | | | | |
| 786-0 | 42.8 | >100 | 15.3 | >100 | <10 | 19.4 | <10 | 13.5 | 618 | 63.5 |
| A498 | 33.2 | 6.69 | <10 | NA | <10 | <0.01 | 10.4 | 1.50 | 343 | 9.32 |
| ACHN | 81.3 | >100 | 145 | >100 | <10 | 62.5 | <10 | >100 | 705 | >100 |
| CAKI-1 | 42.6 | >100 | 50.2 | >100 | <10 | >100 | <10 | >100 | 316 | >100 |
| U0-31 | 92.3 | >100 | 20.0 | >100 | <10 | 25.1 | <10 | 24.6 | 661 | 72.7 |
| Prostate Cancer | | | | | | | | | | |
| PC-3 | 45.8 | >100 | 41.5 | >100 | <10 | 35.2 | 18.4 | 39.4 | 255 | 43.7 |
| DU-145 | 26.6 | NA | 44.8 | >100 | <10 | NA | 25.0 | >100 | 346 | >100 |
| Breast Cancer | | | | | | | | | | |
| MCF7 | 26.9 | >100 | 24.5 | >100 | <10 | >100 | <10 | 37.9 | 76.8 | >100 |
| MDA-MB-231/ATCC | 94.7 | >100 | 46.0 | >100 | <10 | >100 | 44.4 | >100 | 529 | 31.5 |
| HS 5781 | NA | >100 | 40.9 | >100 | <10 | >100 | 668 | 64.2 | 442 | >100 |
| MDA-MB-468 | 34.6 | 26.0 | 23.3 | 0.08 | <10 | 22.4 | 14.7 | 30.5 | 226 | 25.8 |

$^a$GI$_{50}$: 50% Growth inhibition, concentration of drug resulting in a 50% reduction in net protein increase compared with control cells.
$^b$TGI: 100% Growth inhibition, concentration of drug resulting in a 100% reduction in net protein increase compared with control cells The five compounds selected for the full dose response studies have very effective GI$_{50}$ and TGI (Total Growth Inhibition) values against a variety of human tumor cell lines. All the compounds have LD$_{50}$ values>100 µM against most of the human cancer cell lines implying the compounds are anti-proliferative. Specifically, Example 5 had impressive GI$_{50}$ values of less than 10 nM against almost all the cell lines except melanoma cancer cell line UACC-62, colon cancer cell lines COLO 205 and HCC-2998. This compound also showed potent TGI values of <10 nM against CNS cancer cell line SF-539, melanoma cell MDA-MB-435, ovarian cancer cell line OVCAR-3 and renal cancer cell line A498. Example 4 and Example 6 have <10 nM GI$_{50}$ values against Leukemia cancer cell lines K-562, SR, non-small lung cancer cell line HOP-92, colon cancer cell lines HCT-116, HCT-15, melanoma cancer lines M14, UACC-62, ovarian cancer cell line NCI/ADR-RES and renal cancer cell line A498. Melanoma cancer cell line MDA-MB-435 appeared to be sensitive to the growth inhibitory effects of Example 4; and Example 5 exhibited a TGI value of <10 nM against ovarian cancer cell line OVCAR-3.

Some of these compounds were also screened against breast cancer cell line Hs578T. Briefly, Hs578T cells were seeded at 3,000 cells per well into 96-well plates and incubated overnight at 37° C. in DMEM (Dulbecco's Modified Eagle's Medium) containing 10% FBS (Fetal Bovine Serum) medium. The following day, various concentrations of combretastin analogs, or vehicle, were added to each plate and the plates were then incubated for 48 hours. Then, cells were washed twice with Dulbecco's Phosphate-Buffered Saline (DPBS) pH 7.4 and incubated with 2 µM Calcein-AM for 30 minutes at 25° C. Fluorescence was measured using a 490 nm excitation filter and a 520 nm emission filter. The fluorescence intensity is proportional to the number of viable cells. The fluorescence intensity of control (untreated) cells was taken as 100% viability. The relative cell viability compared to control was calculated by using the following formula:

Cell viability (%)=Fluorescence intensity of treated cells/Fluorescence intensity of untreated cells× 100.

The GI$_{50}$ values (growth inhibition; anti-proliferation) were calculated using Graph Pad prism (San Diego, Calif.) by plotting the percent cell viability as a function of the compound concentration and fit to a four-parameter logistic model. The data represents mean±standard deviation of three independent experiments.

Figure 6A:
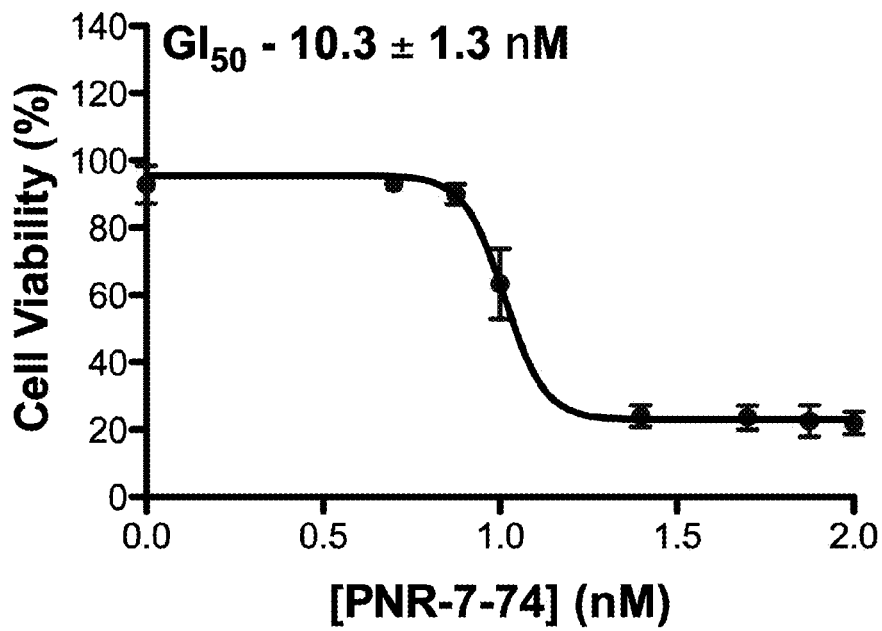
FIG. 6A shows a growth inhibition study for 4-(benzo[b]thiophen-2-yl)-5-(3,4,5-trimethoxyphenyl)-2H-1,2,3-triazole (PNR-7-74) against Hs578T cells. PNR-7-74 is depicted in FIG. 6B.
Figure 6B:
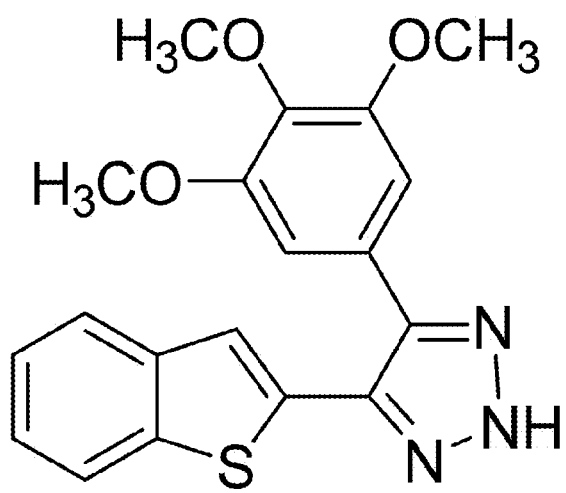
Figure 7A:
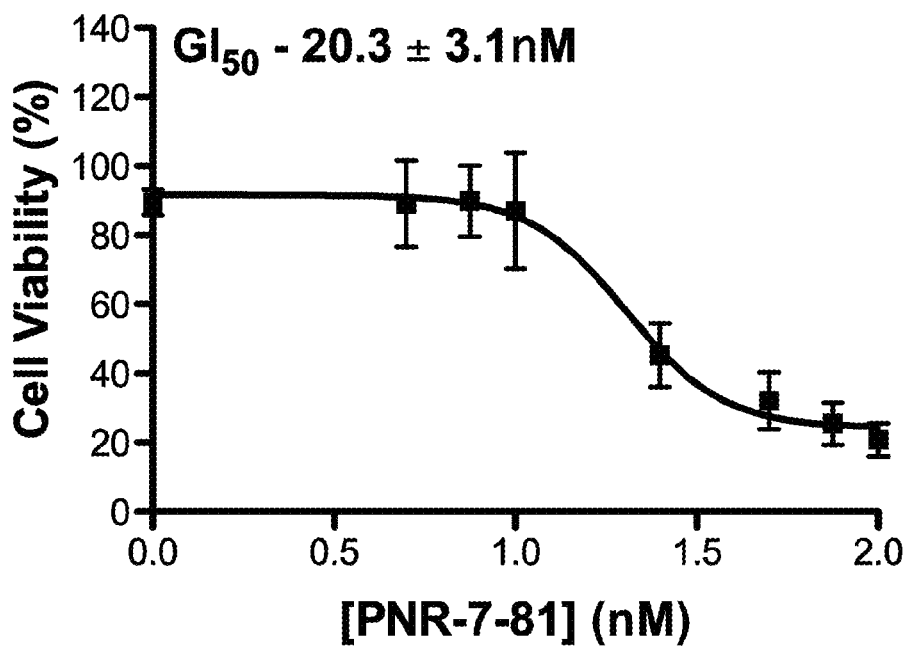
FIG. 7A shows a growth inhibition study for 4-(benzofuran-2-yl)-5-(3,4,5-trimethoxyphenyl)-2H-1,2,3-triazole (PNR-7-81) against Hs578T cells. PNR-7-81 is depicted in FIG. 7B.
Figure 7B:
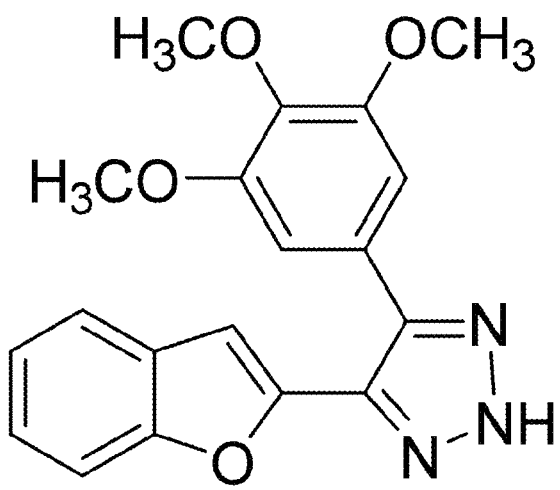
Figure 8A:
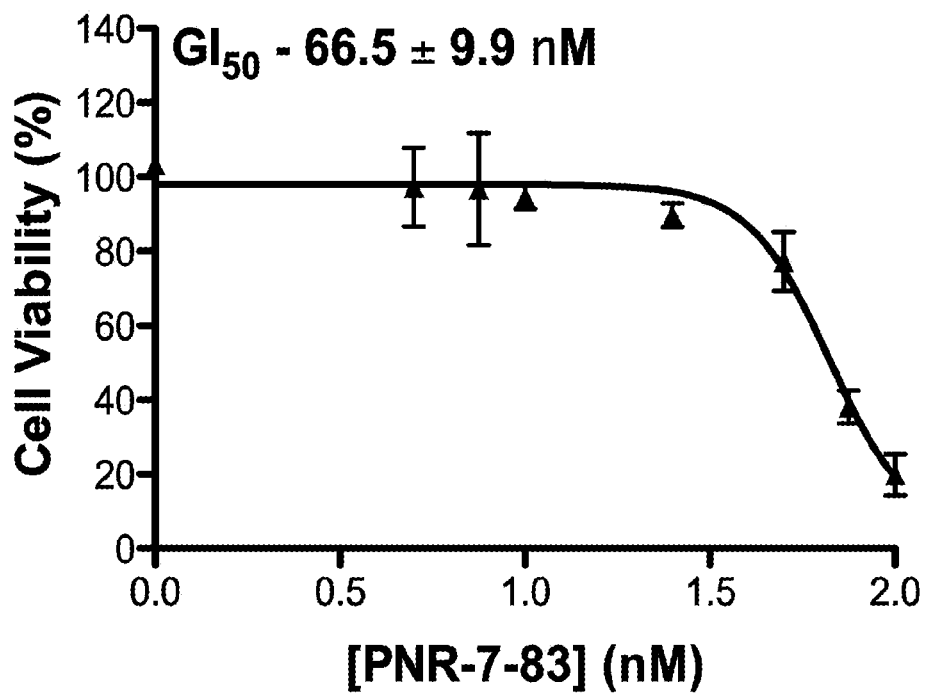
FIG. 8A shows a growth inhibition study for 4-(benzo[b]thiophen-2-yl)-5-(3,5-dimethoxyphenyl)-2H-1,2,3-triazole (PNR-7-83) against Hs578T cells. PNR-7-83 is depicted in FIG. 8B.
Figure 8B:
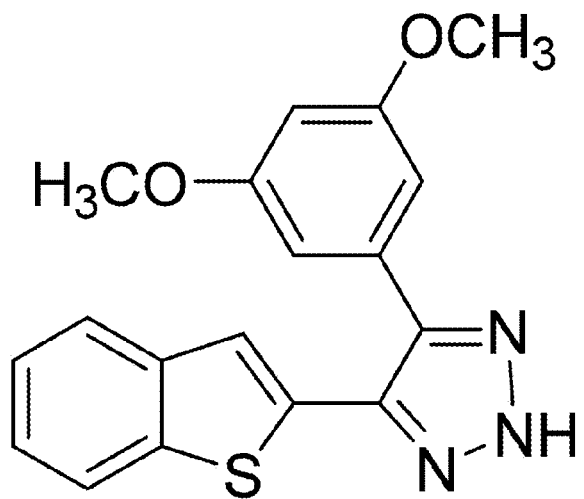
Figure 9B:
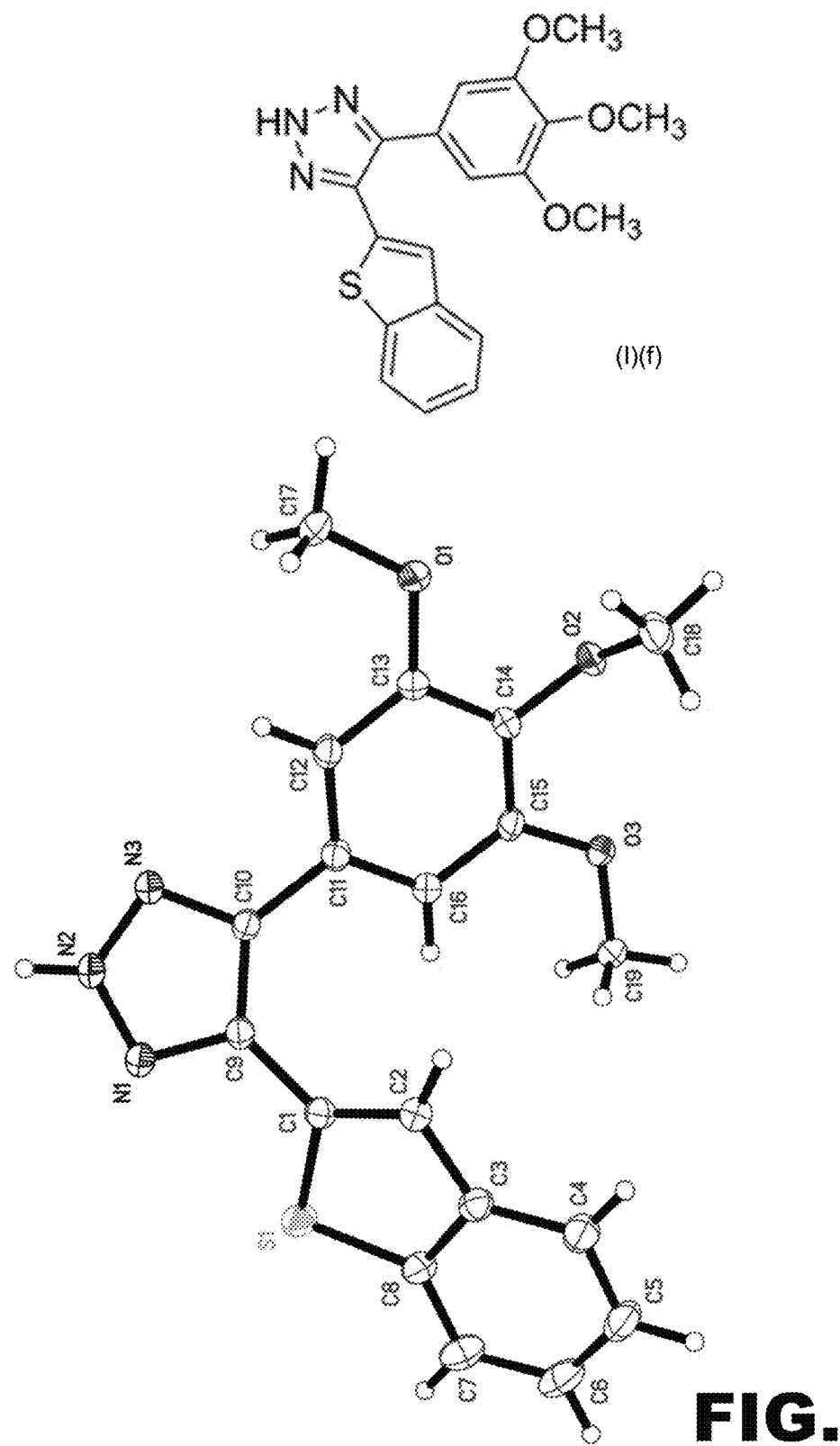

The results of the representative Examples 3-7 are discussed in this embodiment. 4-(benzo[b]thiophen-2-yl)-5-(3, 4,5-trimethoxyphenyl)-2H-1,2,3-triazole (Example 9, PNR-7-74) showed potent cytotoxicity against Hs578T cells with an GI$_{50}$ of 10.3 nM (FIG. 6) and a second analog 4-(benzofuran-2-yl-5-(3,4,5-trimethoxyphenyl)-2H-1,2,3-triazole (Example 10, PNR-7-81) showed very good cytotoxicity against Hs578T cells with an GI$_{50}$ of 20.3 nM (FIG. 7). A third dimethoxy compound, 4-(benzo[b]thiophen-2-yl)-5-(3,5-dimethoxyphenyl)-2H-1,2,3-triazole (Example 11, PNR-7-83) exhibited good cytotoxicity against Hs578T cells with an GI$_{50}$ of 66.5 nM (FIG. 8).

Example 2: Synthesis of 5-(3,4-dichlorophenyl)-4-(3,4-dimethoxyphenyl)-2H-1,2,3-triazole

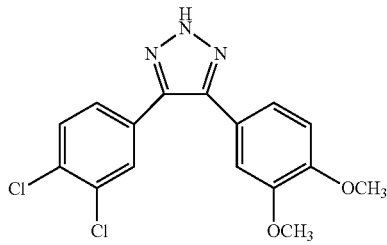 [SMILES: COc1ccc(-c2n[nH]nc2-c2ccc(Cl)c(Cl)c2)cc1OC]

A mixture of (Z)-3-(3,4-dichlorophenyl)-2-(3,4-dimethoxyphenyl)acrylonitrile (100 mg; 1 mmol), sodium azide (58 mg; 3 mmol) and ammonium chloride (48 mg; 3 mmol) was refluxed in DMF/water (4 ml/1 ml) solution for 5 hrs. After the reaction was completed, 12 ml of water was added and the resulting mixture stirred; the final product crashed out of the solution. The precipitate was then filtered and dried to yield the final product: 5-(3,4-dichlorophenyl)-4-(3,4-dimethoxyphenyl)-2H-1,2,3-triazole: yellow solid; $^1$H NMR (400 MHz, DMSO-d$_6$): §3.82 (s, 3H, —OCH$_3$), §3.93 (s, 3H, —OCH$_3$), 6.87-6.89 (d, J=8 Hz, 1H, ArH), 7.05-7.07 (d, J=12 Hz, 2H, ArH), 7.42 (s, 2H, ArH), 7.78 (s, 1H, ArH). $^{13}$C NMR (100 MHz, DMSO-d$_6$): 55.87, 55.96, 111.05, 127.31, 129.80, 129.89, 130.54, 132.60, 132.86, 149.15, 149.754.

Example 3: Synthesis of 4,5-bis(3,4,5-trimethoxyphenyl)-2H-1,2,3-triazole

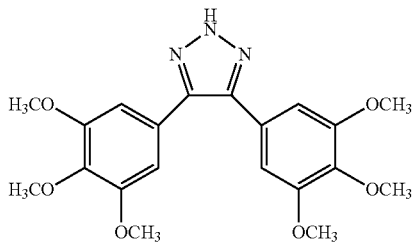 [SMILES: COc1cc(-c2n[nH]nc2-c2cc(OC)c(OC)c(OC)c2)cc(OC)c1OC]

A mixture of (Z)-2,3-bis(3,4,5-trimethoxyphenyl)acrylonitrile (100 mg; 1mmol), sodium azide (50 mg; 3 mmol) and ammonium chloride (42 mg; 3 mmol) was refluxed in DMF/water (4 ml/1 ml) solution for 5 hrs. After the reaction was completed, 12 ml of water was added and the resulting mixture stirred; the final product crashed out of the solution. The precipitate was then filtered and dried to yield the final product: 4,5-bis(3,4,5-trimethoxyphenyl)-2H-1,2,3-triazole: yellow solid; $^1$H NMR (400 MHz, DMSO-d$_6$): §3.77 (s, 12H, —OCH$_3$), 3.88 (s, 6H, —OCH$_2$), 6.85 (s, 4H, ArH). $^{13}$C NMR (100 MHz, DMSO-d$_6$): 56.02, 56.11, 56.19, 60.91, 60.99, 105.47, 125.64, 138.25, 153.27.

Example 4: Synthesis of 2-(5-(3,4,5-trimethoxyphenyl)-2H-1,2,3-triazol-4-yl-quinolinequinoline

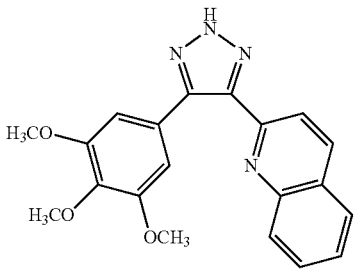 [SMILES: COc1cc(-c2n[nH]nc2-c2ccc3ccccc3n2)cc(OC)c1OC]

A mixture of (Z)-3-(quinolin-2-yl)-2-(3,4,5-trimethoxyphenyl)acrylonitrile (100 mg; 1 mmol), sodium azide (50 mg; 3 mmol) and ammonium chloride (42 mg; 3 mmol) was refluxed in DMF/water (4 ml/1 ml) solution for 5 hrs. After the reaction was completed, 12 ml of water was added and the resulting mixture stirred; the final product crashed out of the solution. The precipitate was then filtered and dried to yield the final product 2-(5-(3,4,5-trimethoxyphenyl)-2H-1,2,3-triazol-4-yl)quinoline: yellow solid; $^1$H NMR (400 MHz, DMSO-d$_6$): §3.47 (s, 6H, —OCH$_3$), 3.81 (s, 3H, —OCH$_3$), 6.65 (s, 2H, ArH), 7.50-7.52 (t, J=8 Hz, 1H, ArH), 7.54-7.56 (d, J=4.4 Hz, 1H, ArH), 7.76-7.77 (t, J=1.6 Hz, 1H, ArH), 7.82-7.84 (d, J=8 Hz, 1H, ArH), 8.27-8.29 (d, J=8.8 Hz, 1H, ArH), 9.03-9.04 (d, J=4.4 Hz, 1H, ArH). $^{13}$C NMR (100 MHz, DMSO-d$_6$): 55.70, 55.79, 60.85, 60.95, 104.47, 104.55, 122.68, 122.76, 124.69, 125.95, 126.66, 127.52, 129.42, 130.21, 138.21, 138.45, 148.15, 149.63, 149.69, 153.24. HRMS (ESI): m/z calcd for C$_{20}$H$_{19}$N$_4$O$_3$ [M-H] 363.1457. found 363.1445.

Example 5: Synthesis of 4-(3,5-dimethoxyphenyl)-5-(4-methoxyphenyl)-2H-1,2,3-triazole

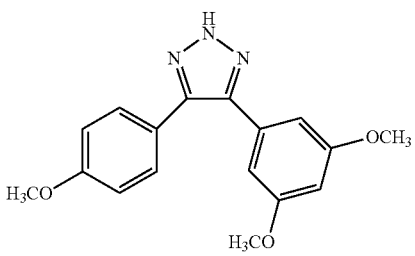 [SMILES: COc1ccc(-c2n[nH]nc2-c2cc(OC)cc(OC)c2)cc1]

A mixture of (Z)-2-(3,5-dimethoxyphenyl)-3-(4-methoxyphenyl)acrylonitrile (100 mg; 1 mmol), sodium azide (50 mg; 3 mmol) and ammonium chloride (42 mg; 3 mmol) was refluxed in DMF/water (4 ml/1 ml) solution for 5 hrs. After the reaction was completed, 12 ml of water was added and the resulting mixture stirred; the final product crashed out of the solution. The precipitate was then filtered and dried to yield the final product 4-(3,5-dimethoxyphenyl)-5-(4-methoxyphenyl)-2H-1,2,3-triazole as a pale yellow solid: $^1$H NMR (400 MHz, DMSO-d$_6$): δ 3.69 (s, 4H, —OCH$_3$), 3.79 (s, 3H, —OCH$_3$), 6.50 (s, 1H, ArH), 6.64 (s, 2H, Ark), 7.00-7.02 (d, J=8 Hz, 2H, ArH), 7.42-7.44 (d, J=8.8 Hz, 2H, ArH). $^{13}$C NMR (100 MHz, DMSO-d$_6$): δ5.36, 56.05, 60.89, 60.99, 105.13, 105.18, 114.03, 125.86, 129.79, 138.07, 153.26, 159.96.

Example 6: Synthesis of 4-(4-methoxyphenyl)-5-(3,4,5-trimethoxyphenyl)-2H-1,2,3-triazole

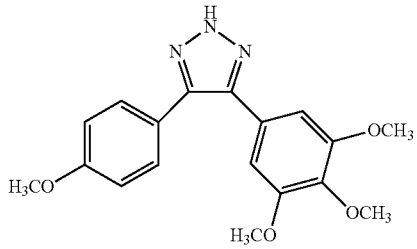 [SMILES: COc1ccc(-c2n[nH]nc2-c2cc(OC)c(OC)c(OC)c2)cc1]

A mixture of (Z)-2-(3,4,5-dimethoxyphenyl)-3-(4-methoxyphenyl)acrylonitrile (100 mg; 1 mmol), sodium azide (50 mg; 3 mmol) and ammonium chloride (42 mg; 3 mmol) was refluxed in DMF/water (4 ml/1 ml) solution for 5 hrs. After the reaction was completed, 12 ml of water was added and the resulting solution stirred; the final product crashed out of the solution. The precipitate was then filtered and dried to yield the final product 4-(4-methoxyphenyl)-5-(3,4,5-trimethoxyphenyl)-2H-1,2,3-triazole as a pale yellow solid: $^1$H NMR (400 MHz, CDCl$_3$-d): δ 3.74 (s, 6H, —OCH$_3$), 3.84 (s, 3H, —OCH$_3$), 3.89 (s, 3H, —OCH$_3$), 6.83 (s, 2H, ArH), 6.91-6.93 (d, J=8.4 Hz, 2H, ArH), 7.51-7.53 (d, J=8 Hz, 2H, ArH). $^{13}$C NMR (100 MHz, CDCl$_3$-d): 55.26, 55.36, 55.96, 56.05, 60.91, 60.99, 105.13, 105.18, 114.03, 125.86, 129.79, 138.07, 153.27, 159.97.

Example 7: Synthesis of 4-(2,3-dihydrobenzo[b][1,4]dioxin-6-yl)-5-(3,4,5-trimethoxyphenyl)-2H-1,2,3-triazole

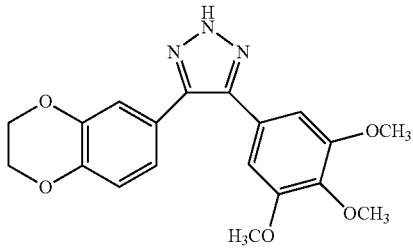 [SMILES: COc1cc(-c2n[nH]nc2-c2ccc3c(c2)OCCO3)cc(OC)c1OC]

A mixture of (Z)-3-(2,3-dihydrobenzo[b][1,4]dioxin-6-yl)-2-(3,4,5-trimethoxyphenyl)acrylonitrile (100 mg; 1 mmol), sodium azide (50 mg; 3 mmol) and ammonium chloride (42 mg; 3 mmol) was refluxed in DMF/water (4 ml/1 ml) solution for 5 hrs. After the reaction was completed, 12 ml of water was added and the resulting mixture stirred; the final product crashed out of the solution. The precipitate was then filtered and dried to yield the final product 4-(2,3-dihydrobenzo[b][1,4]dioxin-6-yl)-5-(3,4,5-trimethoxyphenyl)-2H-1,2,3-triazole as a pale yellow solid: $^1$H NMR (400 MHz, CDCl$_3$-d): δ 3.77 (s, 6H, —OCH$_3$), 3.89 (s, 3H, —OCH$_3$), 4.27-4.30 (dd, J=12.4 Hz, 4H, CH$_2$), 6.85 (s, 2H, ArH), 6.87-6.89 (d, J=8 Hz, 1H, ArH), 7.05-7.07 (dd, J=10 Hz, 1H, ArH), 7.15-7.16 (d, J=1.6 Hz, 1H, ArH. $^{13}$C NMR (100 MHz, CDCl3-d): 55.99, 56.09, 60.91, 60.99, 64.28, 64.47, 105.24, 105.28, 117.42, 121.81, 138.19, 143.59, 144.09, 153.27.

Example 8: Synthesis of 4-(benzo[d][1,3]dioxol-5-yl)-5-(3,4,5-trimethoxyphenyl)-2H-1,2,3-triazole

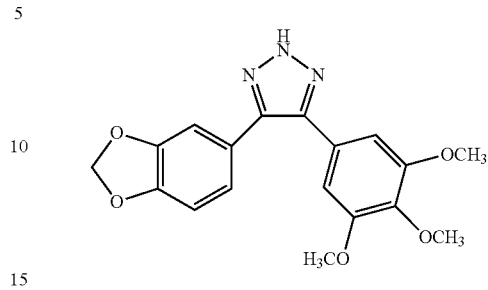

A mixture of (Z)-3-(benzo[d][1,3]dioxol-5-yl)-2-(3,4,5-trimethoxyphenyl)acrylonitrile (100 mg; 1 mmol), sodium azide (50 mg; 3 mmol) and ammonium chloride (42 mg; 3 mmol) was refluxed in DMF/water (4 ml/1 ml) solution for 5 hrs. After the reaction was completed, 12 ml of water was added and the resulting mixture was stirred; the final product crashed out of the solution. The precipitate was then filtered and dried to yield the final product 4-(benzo[d][1,3]dioxol-5-yl)-5-(3,4,5-trimethoxyphenyl)-2H-1,2,3-triazole as a pale yellow solid: $^1$H NMR (400 MHz, CDCl$_3$-d): δ 3.75 (s, 6H, —OCH$_3$), 5.99 (s, 2H, CH$_2$), 6.47-6.49 (d, J=4.4 Hz, 1H, ArH), 6.73-6.74 (d, J=2.4 Hz, 2H, ArH), 6.81-6.83 (d, J=8.8 Hz, 1H, ArH), 7.05-7.07 (d, J=6.4 Hz, 2H, ArH). $^{13}$C NMR (100 MHz, CDCl$_3$-d): 55.34, 55.43, 55.52, 101.05, 101.13, 101.25, 101.32, 106.12, 106.18, 108.51, 108.80, 122.39, 131.91, 147.82, 147.98, 160.87.

Example 9: Synthesis of 4-(benzo[b]thiophen-2-yl)-5-(3,5-dimethoxyphenyl)-2H-1,2,3-triazole (Procedure B)

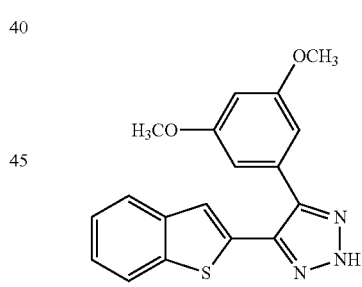

Trimethylsilyl azide (3.45 g, 0.03 mol) in N,N-dimethylformamide (5) was added to (Z)-3-(benzo[b]thiophen-2-yl)-2-(3,5-dimethoxyphenyl) acrylonitrile (3.21 g; 0.01 mol) followed by addition of aqueous HCl (0.1 mmol). The resulting reaction mixture was heated to 130-135° C. and stirred. After completion of the reaction, the reaction mixture was cooled to 20° C., water (10 ml) and hydrochloric acid (2.0 g, 35% W/W) were added slowly over 30 min and the slurry obtained was stirred for 60 min. The resulting solid was filtered, washed with cold ethanol (5 ml) and dried to afford the pure product, 4-(benzo[b]thiophen-2-yl)-5-(3,5-dimethoxyphenyl)-2H-1,2,3-triazole, as a pale yellow powder (3.0 g, 89% yield). MF: C$_{18}$H$_{15}$N$_3$O$_2$S, MW: 337.40, mp: 76-78° C., $^1$H NMR (CDCl$_3$): δ 3.72 (s, 6H, 2×OCH$_3$), 6.52 (s, 1H), 6.81 (s, 2H), 7.30-7.31 (d, J=2.8 Hz, 2H), 7.50 (s, 1H), 7.67 (s, 1H), 7.77 (s, 1H) ppm; $^{13}$C NMR (CDCl₃): δ 55.72, 102.06, 106.87, 122.43, 123.37, 124.10, 124.12, 124.76, 125.12, 125.10, 131.30, 132.22, 140.03, 161.24 ppm.

Example 10: Synthesis of 4-(benzo[b]thiophen-2-yl)-5-(3,4,5-trimethoxyphenyl)-2H-1,2,3-triazole (PNR-7-74)

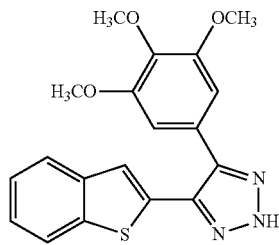 [SMILES: COc1cc(-c2n[nH]nc2-c2cc3ccccc3s2)cc(OC)c1OC]

Sodium azide (3.45 g, 0.03 mol) in DMSO (5 ml) was added to (Z)-3-(benzo[b]thiophen-2-yl)-2-(3,4,5-trimethoxyphenyl)acrylonitrile (3.5 g; 0.01 mol) followed by addition of proline (20 mol %). The resulting reaction mixture was heated to 100-105° C. and stirred. After completion of the reaction, the reaction mixture was cooled to 20° C., water (10 ml) and the slurry obtained was stirred for 60 min. The resulting solid was filtered, washed with cold ethanol (5 ml) and dried to afford the pure product 4-(benzo[b]thiophen-2-yl)-5-(3,4,5-trimethoxyphenyl)-2H-1,2,3-triazole, as a pale yellow powder (3.2 g, 87% yield). MF: C₁₉H₁₇N₃O₃S, MW: 367.42, mp: 189-191 C, ¹H NMR (CDCl₃): δ 3.82 (s, 6H, 2×OCH₃), 3.95 (s, 3H, —OCH₃), 6.94 (s, 2H), 7.34-7.36 (m, 2H), 7.56 (s, 1H), 7.71-7.73 (m, 1H), 7.83-7.86 (m, 1H) ppm, ¹³C NMR (CDCl₃): δ 56.12, 60.97, 105.86, 122.14, 122.24, 123.11, 123.74, 123.85, 124.60, 125.01, 138.75, 139.73, 139.78, 153.46 ppm.

Example 11: Synthesis of 4-(benzofuran-2-yl)-5-(3,4,5-trimethoxyphenyl)-2H-1,2,3-triazole

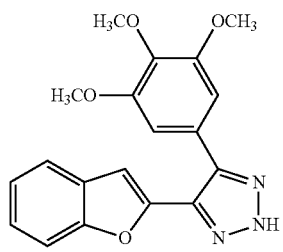 [SMILES: COc1cc(-c2n[nH]nc2-c2cc3ccccc3o2)cc(OC)c1OC]

Trimethylsilyl azide (3.45 g, 0.03 mol) in N,N-dimethylformamide (5 ml) was added to (Z)-3-(benzofuran-2-yl)-2-(3,4,5-trimethoxyphenyl)acrylonitrile (3.3 g; 0.01 mol) followed by addition of aqueous HCl (0.1 mmol). The resulting reaction mixture was heated to 130-135° C. and stirred. After completion of the reaction, the reaction mixture was cooled to 20° C., water (10 ml) and hydrochloric acid (2.0 g, 35% W/W) were added slowly over 30 min and the slurry obtained was stirred for 60 min. The resulting solid was filtered, washed with cold ethanol (5 ml) and dried to afford the pure product 4-(benzofuran-2-yl)-5-(3,4,5-trimethoxyphenyl)-2H-1,2,3-triazole, as a pale yellow powder (2.95 g, 85% yield). MF: C₁₉H₁₇N₃O₄, MW: 351.36, mp: 158-160° C., ¹H NMR (CDCl₃): δ 3.85 (s, 6H, 2×OCH₃), 3.94 (s, 3H, —OCH₃), 7.01 (s, 2H), 7.10 (s, 1H), 7.24-7.28 (m, 2H), 7.31-7.34 (t, J=6.8 and 15.2 Hz, 1H), 7.51-7.53 (d, J=8 Hz, 1H), 7.58-7.60 (d, J=7.6 Hz, 1H) ppm; ¹³C NMR (CDCl₃): δ 56.10, 60.92, 105.76, 111.22, 121.24, 121.39, 123.33, 125.17, 128.15, 138.74, 153.37, 154.71 ppm.

Example 12: 4-(benzo[b]thiophen-2-yl)-5-(3,5-dimethoxyphenyl)-2H-1,2,3-triazole (PNR-7-83)

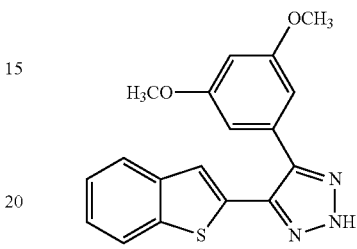

Potassium azide (2.43 g, 0.03 mol) in N,N-dimethylformamide (5 ml) was added to (Z)-3-(benzo[b]thiophen-2-yl)-2-(3,4,5-trimethoxyphenyl)acrylonitrile (3.5 g; 0.01 mol) followed by addition of aqueous HCl (0.1 mmol). The resulting reaction mixture was heated to 130-135° C. and stirred. After completion of the reaction, the reaction mixture was cooled to 20° C., water (10 ml) and hydrochloric acid (2.0 g, 35% W/W) were added slowly over 30 min and the slurry obtained was stirred for 60 min. The solid was filtered, washed with cold ethanol (5 ml) and dried to afford the pure product 4-(benzo[b]thiophen-2-yl)-5-(3,4,5-trimethoxyphenyl)-2H-1,2,3-triazole, as a pale yellow powder (2.8 g, 76% yield). MF: C₁₉H₁₇N₃O₃S, MW: 367.42, mp: 189-191 C, ¹H NMR (CDCl₃): δ 3.82 (s, 6H, 2×OCH₃), 3.95 (s, 3H, —OCH₃), 6.94 (s, 2H), 7.34-7.36 (m, 2H), 7.56 (s, 1H), 7.71-7.73 (m, 1H), 7.83-7.86 (m, 1H) ppm, ¹³C NMR (CDCl₃): δ 56.12, 60.97, 105.86, 122.14, 122.24, 123.11, 123.74, 123.85, 124.60, 125.01, 138.75, 139.73, 139.78, 153.46 ppm.

Example 13: 4-(benzo[b]thiophen-2-yl)-5-(3,4,5-trimethoxyphenyl)-2H-1,2,3-triazole (PNR-7-74)

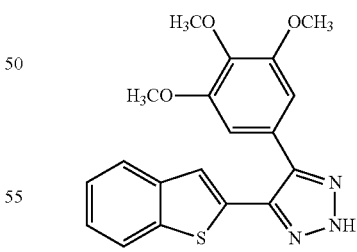

Potassium azide (2.43 g, 0.03 mol) in N,N-dimethylformamide (5 ml) was added to (Z)-3-(benzo[b]thiophen-2-yl)-2-(3,4,5-trimethoxyphenyl)acrylonitrile (3.5 g; 0.01 mol) followed by addition of aqueous HCl (0.1 mmol). The resulting reaction mixture was heated to 130-135° C. and stirred. After completion of the reaction, the reaction mixture was cooled to 20° C., water (10 ml) and hydrochloric acid (2.0 g, 35% W/W) were added slowly over 30 min and the slurry obtained was stirred for 60 min. The solid was filtered, washed with cold ethanol (5 ml) and dried to afford the pure product 4-(benzo[b]thiophen-2-yl)-5-(3,4,5-trimethoxyphenyl)-2H-1,2,3-triazole, as a pale yellow powder (2.8 g, 76% yield). MF: $C_{19}H_{17}N_3O_3S$, MW: 367.42, mp: 189-191 C, $^1$H NMR (CDCl$_3$): δ 3.82 (s, 6H, 2×OCH$_3$), 3.95 (s, 3H, —OCH$_3$), 6.94 (s, 2H), 7.34-7.36 (m, 2H), 7.56 (s, 1H), 7.71-7.73 (m, 1H), 7.83-7.86 (m, 1H) ppm, $^{13}$C NMR (CDCl$_3$): δ 56.12, 60.97, 105.86, 122.14, 122.24, 123.11, 123.74, 123.85, 124.60, 125.01, 138.75, 139.73, 139.78, 153.46 ppm.

Example 14: Synthesis of 4-(3,4-dichlorophenyl)-5-(3,4-dimethoxyphenyl)-2-methyl-2H-1,2,3-triazole

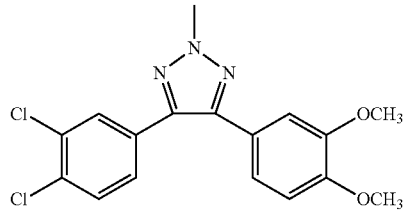 [SMILES: COc1ccc(-c2nn(C)nc2-c2ccc(Cl)c(Cl)c2)cc1OC]

Refluxing a mixture of 4,5-bis(3,4,5-trimethoxyphenyl)-2H-1,2,3-triazole (1 mmol), $K_2CO_3$ (10 mmol) and MeI (2 mmol) in 10 volumes of acetone for 5 hrs yielded 4-(3,4-dichlorophenyl)-5-(3,4-dimethoxyphenyl)-2-methyl-2H-1,2,3-triazole. 2M HCl was used to quench the reaction and rota evaporated. The residue purified by ethyl acetate/hexane flash column chromatography to yield 4-(3,4-dichlorophenyl)-5-(3,4-dimethoxyphenyl)-2-methyl-2H-1,2,3-triazole as a pale yellow solid with 85% yield. $^1$H NMR (400 MHz, CDCl$_3$-d): δ 3.83 (s, 3H, —OCH$_3$), 3.92 (s, 3H, —OCH$_3$), 4.25 (s, 3H, —CH$_3$), 6.86-6.88 (d, J=8 Hz, 1H, ArH), 7.05-7.07 (d, J=15.2 Hz, 2H, ArH), 7.42-7.26 (d, J=16.8 Hz, 2H, ArH), 7.74-7.74 (d, J=1.6 Hz, 1H, ArH). $^{13}$C NMR (100 MHz, CDCl$_3$-d): 41.98, 56.08, 111.40, 121.07, 123.09, 127.45, 129.97, 130.59, 131.376, 132.41, 132.91, 141.99, 144.87, 149.25, 149.63.

Example 15: In Vivo Anti-Leukemic Activity with Compound 8

Figure 10:
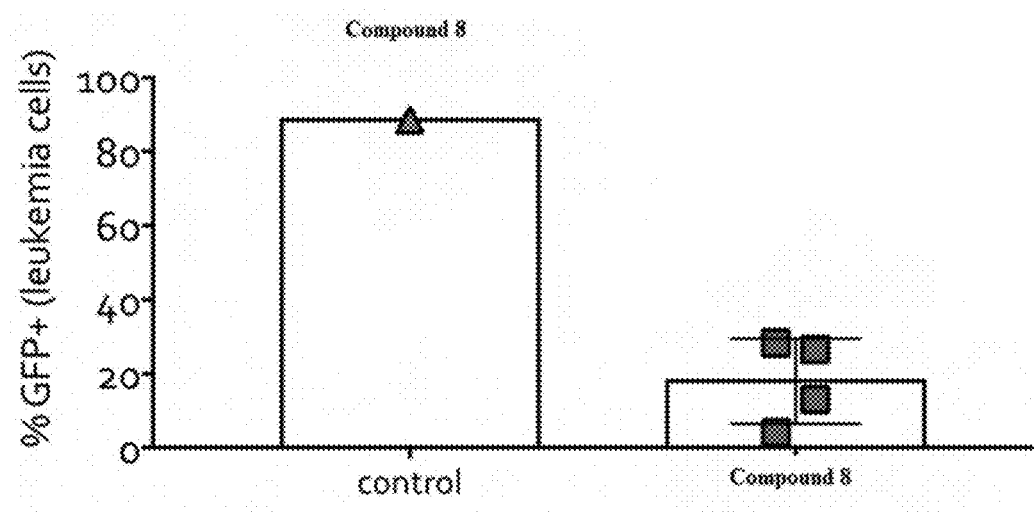
FIG. 10 show bone marrow content of AML stem cells in normal (control) and Compound 8-treated mice.
Figure 11A:
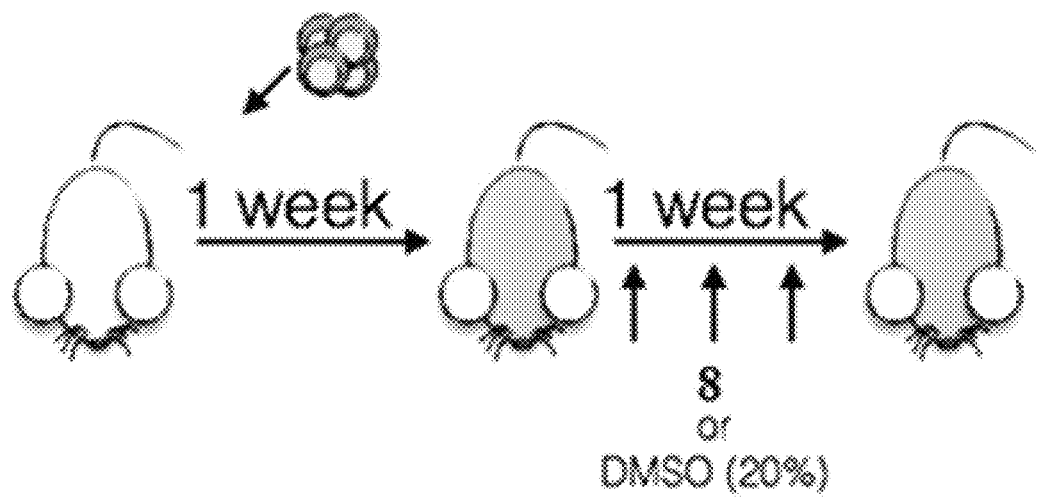
FIG. 11A, FIG. 11B and FIG. 11C show in vivo data demonstrating that Compound 8 has anti-leukemic activity.
Figure 11B:
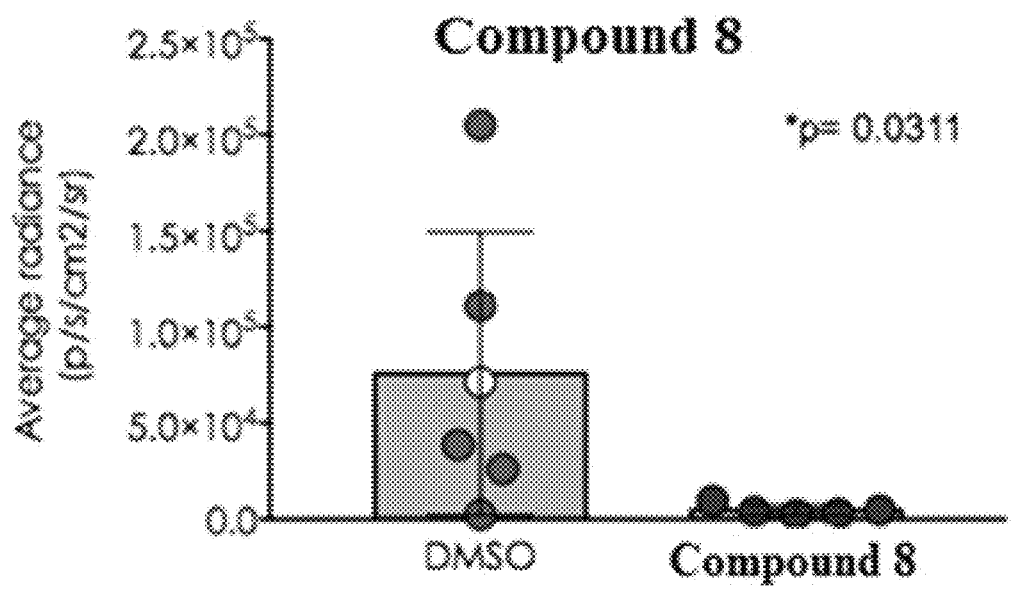
Figure 11C:
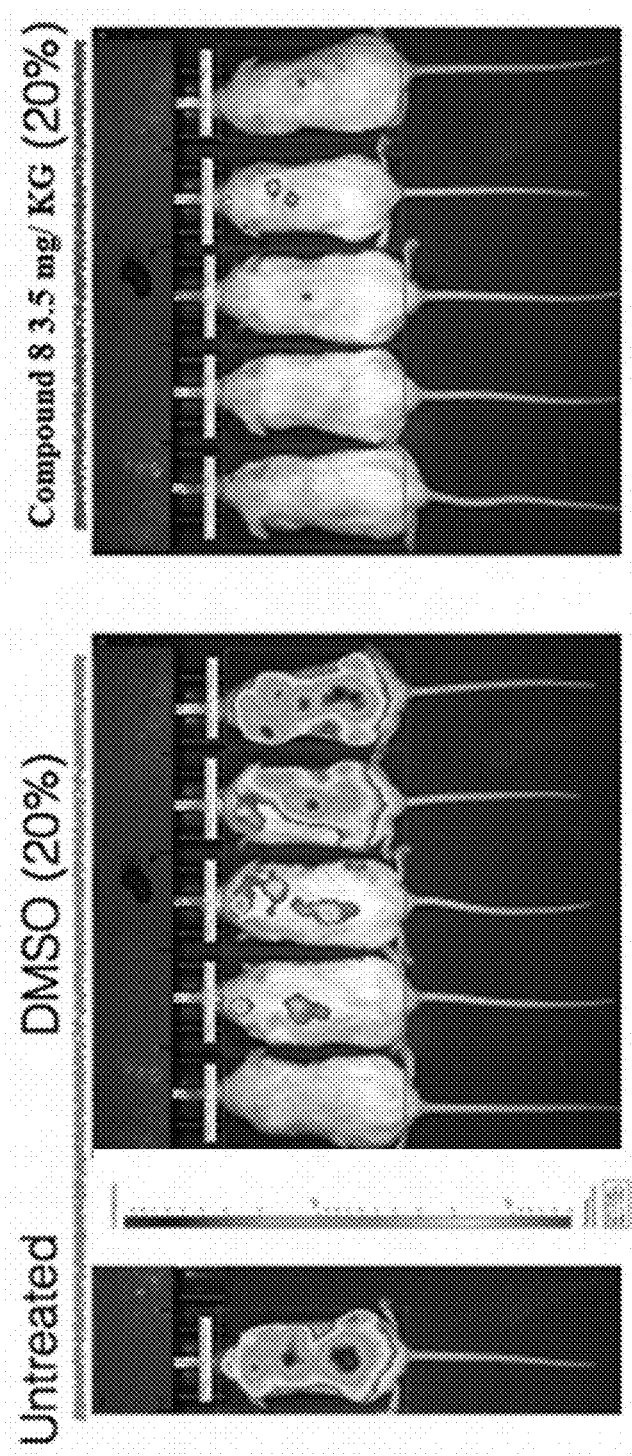

The anti-leukemic activity of Compound 8 (FIG. 1) was evaluated in vivo. GFP expressing leukemia cells were injected into mice. One week post injection, mice were treated with Compound 8 at 3.5 mg/kg or DMSO (control) (FIG. 11A). Mice were imaged one week later. FIG. 11C shows that mice treated with Compound 8 exhibited significant tumor shrinkage relative to DMSO and untreated mice. A direct quantification of average radiance revealed a significant reduction in leukemia cells (FIG. 11B). Further, bone marrow was isolated and the percent of GFP expressing AML stem cells was quantitated. A significant reduction in AML stem cells was observed in Compound 8-treated mice (FIG. 10). Accordingly, Compound 8 demonstrates significant anti-leukemic activity in an in vivo mouse model.

What is claimed is:

1. A compound, the compound of Formula (I):

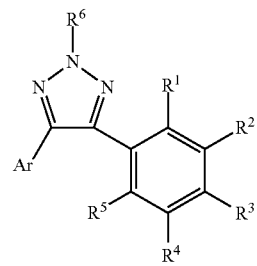

wherein:

$R^1$, $R^5$ and $R^6$ are hydrogen and $R^2$, $R^3$, and $R^4$ are independently chosen from hydrogen, methoxy, and hydroxyl, with the proviso that at least two of $R^2$, $R^3$, and $R^4$ are methoxy; and Ar is an aryl or substituted aryl group.

2. The compound of claim 1, wherein Ar is chosen from phenyl, benzyl, substituted benzyl, benzoyl, substituted benzoyl, naphthyl, substituted naphthyl, naphthoyl, substituted naphthoyl, benzenesulphonyl, substituted benzenesulphonyl, heteroaryl; substituted heteroaryl, aroyl, heteroaroyl.

3. The compound of claim 1, wherein the compound is Formula (I)(a):

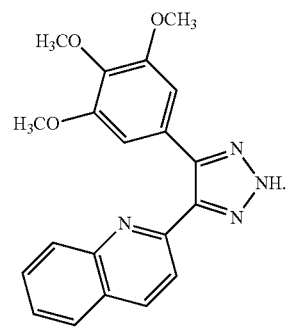

4. The compound of claim 1, wherein the compound is Formula (I)(b):

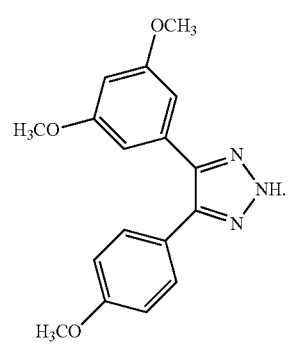

5. The compound of claim 1, wherein the compound is Formula (I)(c):

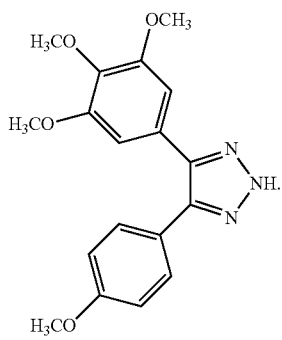

(I)(c)

6. The compound of claim 1, wherein the compound is Formula (I)(d):

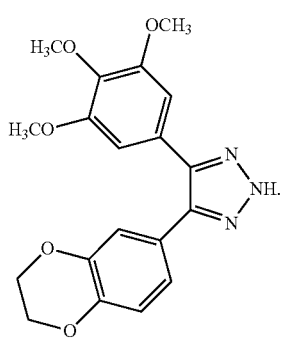

(I)(d)

7. The compound of claim 1, wherein the compound is Formula (I)(e):

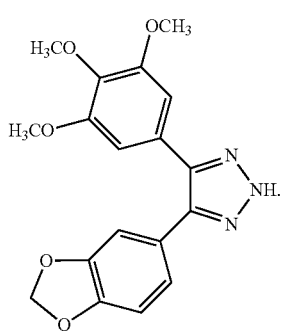

(I)(e)

8. The compound of claim 1, wherein the compound is Formula (I)(f):

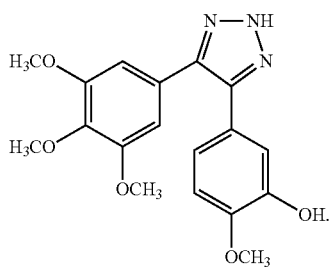

(I)(f)

9. A pharmaceutical composition comprising a compound of Formula (I):

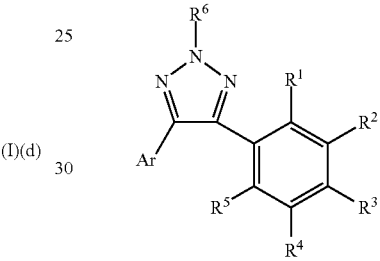

(I)

wherein:

$R^1$, $R^5$, and $R^6$ are hydrogen and $R^2$, $R^3$, and $R^4$ are independently chosen from hydrogen, methoxy, and hydroxyl, with the proviso that at least two of $R^2$, $R^3$, and $R^4$ are methoxy; and Ar is an aryl or substituted aryl group.

10. The pharmaceutical composition of claim 9, wherein the compound of Formula (I) is selected from the group comprising Formula (I)(a), (I)(b), (I)(c), (I)(d), (I)(e), and (I)(f).

11. A compound, the compound selected from the group consisting of:

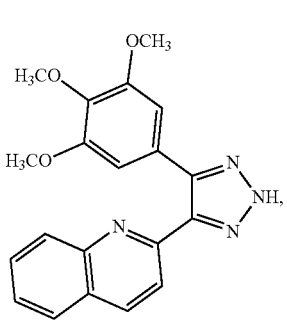

(I)(a)

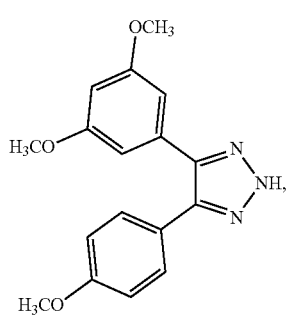
(I)(b)
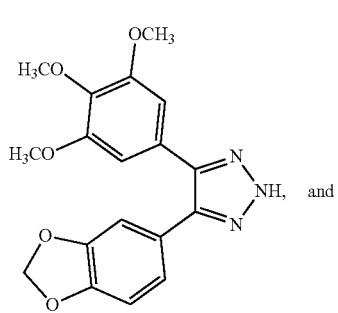
(I)(e)
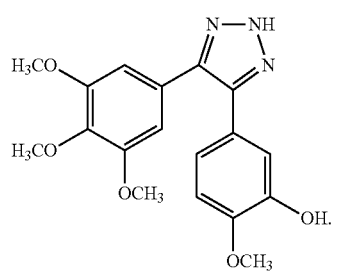
(I)(c)
(I)(d)
(I)(f)
* * * * *